US009243257B2

(12) United States Patent
Takagi et al.

(10) Patent No.: US 9,243,257 B2
(45) Date of Patent: Jan. 26, 2016

(54) TRANSCRIPTIONAL REPRESSOR PEPTIDES AND GENES FOR THE SAME

(75) Inventors: Masaru Takagi, Tsukuba (JP); Miho Ikeda, Tsukuba (JP)

(73) Assignee: NATIONAL INSTITUTE OF ADVANCED INDUSTRIAL SCIENCE AND TECHNOLOGY, Tokyo (JP)

(*) Notice: Subject to any disclaimer, the term of this patent is extended or adjusted under 35 U.S.C. 154(b) by 807 days.

(21) Appl. No.: 12/921,735

(22) PCT Filed: Mar. 12, 2009

(86) PCT No.: PCT/JP2009/054718
§ 371 (c)(1),
(2), (4) Date: Sep. 9, 2010

(87) PCT Pub. No.: WO2009/113603
PCT Pub. Date: Sep. 17, 2009

(65) Prior Publication Data
US 2011/0035846 A1  Feb. 10, 2011

(30) Foreign Application Priority Data
Mar. 12, 2008  (JP) .................. 2008-062113

(51) Int. Cl.
C12N 15/82   (2006.01)
C12N 15/62   (2006.01)
C07K 5/10    (2006.01)
C07K 4/10    (2006.01)
C07K 2/00    (2006.01)
C07K 7/06    (2006.01)
(Continued)

(52) U.S. Cl.
CPC .......... *C12N 15/8216* (2013.01); *C07K 5/1005* (2013.01); *C07K 7/06* (2013.01); *C07K 7/08* (2013.01); *C12N 15/62* (2013.01); *C12N 15/827* (2013.01); *C12N 15/8217* (2013.01); *C12N 15/8261* (2013.01)

(58) Field of Classification Search
USPC ...................................................... 800/278
See application file for complete search history.

(56) References Cited

U.S. PATENT DOCUMENTS 7,030,211 B1    4/2006  Gaudernack et al.
7,342,148 B2 *  3/2008  Takagi et al. .................. 800/295
2003/0233670 A1 * 12/2003  Edgerton et al. .............. 800/278
(Continued)

FOREIGN PATENT DOCUMENTS

JP   2001-269176   10/2001
JP   2001-269177   10/2001
(Continued)

OTHER PUBLICATIONS

Kagaya et al., RAV1 a novel DNA-binding protein, binds to bipartite recognition sequence through two distinct DNA-binding domains uniquely found in higher plants, 27 Nucleic Acids Research No. 2, 470-478 (1999).*
(Continued)

Primary Examiner — Shubo (Joe) Zhou
Assistant Examiner — Ashley K Buran
(74) Attorney, Agent, or Firm — Casimir Jones, S.C.

(57) ABSTRACT

Provided is a peptide which is capable of repressing transcription in a plant and which can be used in the CRES-T (a simple and widely applicable means for repressing gene transcription). Also provided is a gene encoding the peptide.

7 Claims, 4 Drawing Sheets

(51) Int. Cl.
C07K 7/08 (2006.01)
C07K 5/103 (2006.01)

(56) References Cited

U.S. PATENT DOCUMENTS

2004/0216190 A1* 10/2004 Kovalic .................... 800/289
2006/0106196 A1   5/2006 Gaudernack et al.

FOREIGN PATENT DOCUMENTS

| | | |
|---|---|---|
| JP | 2001-269178 | 10/2001 |
| JP | 2001-269179 | 10/2001 |
| JP | 2001-292776 | 10/2001 |
| JP | 2001-292777 | 10/2001 |
| JP | 2002-520293 A | 7/2002 |

OTHER PUBLICATIONS

Nakano et al., Genome-wide analysis of the ERF gene family in Arabidopsis and Rice, 140 Plant Physiology, 411-432 (2006).*
Kagaya et al., RAV1, a novel DNA-binding protein, binds to bipartite recognition sequence through two distinct DNA-binding domains uniquely found in higher plants, 27 Nucleic Acids Research No. 2, 470-478 (1999).*
Santos-Mendoza et al., Deciphering gene regulatory networks that control seed development and maturation in Arabidpsis, 54 Plant Journal, 608-620 (2008), published online Feb. 14, 2008).*
Hu et al., Arabidopsis RAV1 is down-regulated by brassinosteroid and may act as a negative regulator during plant development, 14 Cell Research No. 1, 8-15 (2004).*
Ohta et al. (Repression domains of Class II ERF transcriptional repressors share an essential motif for active repression, 13 Plant Cell, 1959-1968 (2001).*
Hiratsu et al. (Dominant repression of target genes by chimeric repressors that include the EAR motif, a repression domain, in Arabidopsis, 34 Plant Journal, 733-739 (2003).*
Ozkaynak et al., The yeast ubiquitin genes: a family of natural gene fusions, 6 EMBO Journal No. 5, 1429-1439 (1987).*
Pařenicová et al., Molecular and Phylogenetic Analysis of the Complete MADS-Box Transcription Factor Family in Arabidopsis: New Openings to the MADS World, 15 Plant Cell, 1538-1551 (2003).*
Olsen et al., NAC transcription factors: structurally distinct, functionally diverse, 10 Trends in Plant Science No. 2, 79-87 (2005).*
Shiu et al., Transcription Factor Families Have Much Higher Expansion Rates in Plants than in Animals, 139 Plant Physiology, 18-26 at Table 1 on 19 (2005).*
Suzuki et al., (Viviparous1 Alters Global Gene Expression Patterns through Regulation of Abscisic Acid Signaling, 132 Plant Physiology, 1664-1677 (2003)).*
Hauser et al., Trichome Districution in Arabidopsis thaliana and its Close Relative Arabidopsis lyrata: Molecular Analysis of the Candidate Gene GLABROUS1, 18 Mol Biol Evol. No. 9, 1754-1763 (2001), describing GLI as a MYB transcription factor).*
Ikeda et al. (A novel group of transcriptional repressors in Arabidpsis, 50 Plant Cell Physiol No. 5, 970-975 (2009)).*
Bolduc et al., The Maize Transcription Factor KNOTTED1 Directly Regulates the Gibberellin Catabolism Gene ga2ox1, 21 Plant Cell, 1647-1658 at 1647 (2009)).*
Ohta, Masaru, et al., "Repression Domains of Class II ERF Transcriptional Repressors Share an Essential Motif for Active Repression," The Plant Cell, vol. 13, No. 8, pp. 1959-1968, Aug. 2001.

Mitsuda, Nobutaka, et al., "Efficient Production of Male and Female Sterile Plants by Expression of a Chimeric Repressor in Arabidopsis and Rice," Plant Biotechnology Journal (2006) 4, pp. 325-332.
Hiratsu, Keiichiro, et al., "Dominant Repression of Target Genes by Chimeric Repressors that Include the EAR Motif, a Repression Domain, in Arabibopsis," The Plant Journal (2003) 34, pp. 733-739.
Rubio-Somoza, Ignacio, et al., "HvMCB1, a R1MYB Transcription Factor from Barley with Antagonistic Regulatory Functions During Seed Development and Germination," The Plant Journal (2006) 45, pp. 17-30.
Ikeda, Miho, et al., "Shiroinunazuna ni Okeru Shinki Repression Domain no Dotei to, sore o Motsu Tensha Yokusei Inshi no Kino Kaiseki", Dai 49 Kai Proceedings of the Annual Meeting of the Japanese Society of Plant Physiologists, Mar. 15, 2008, p. 102, 1aB08(008), partial English translation attached.
Ikeda, Miho, et al., "WUS Family ni Kyotsu suru Tensha Yokusei Domain no Kaiseki", Dai 25 Kai Nippon Shokubutsu Bunshi Seibutsu Gakkai Taikai-Symposium Koen Yoshishu, Aug. 8, 2007, p. 145, 2Ap9, partial English translation attached.
Hiratsu K, Matsui K, Koyama T. Ohme-takagi M. Dominant repression of target genes by chimeric repressors that include the EAR motif, a repression domain, in Arabidopsis. Plant J. 34: 733-739. 2003.
Fujita M, Fujita Y, Maruyama K, Seki M, Hiratsu K, Ohme-Takagi M, Tran LP, Yamaguchi-Shinozaki K, Shinozaki K. A dehydration-induced NAC protein, RD26, is invoved in a novel ABA-dependent stress-signaling pathway. Plant J. 39: 863-876. 2004.
Mitsuda N, Seki M, Shinozaki K, Ohme-Takagi M. The NAC transcription factors NST1 and NST2 of Arabidopsis regulate secondary wall thickenings and are required for anther dehiscence. Plant Cell. 17: 2993-3006. 2005.
Fujita Y, Fujita M, Satoh R, Maruyama K, Parvez MM, Seki M, Hiratsu K, Ohme-Takagi M, Tran LP, Shinozaki K, Yamaguchi-Shinozaki K. AREB1 is a transcription activator of novel ABRE-dependent ABA signaling that enhances drought stress tolerance in Arabidopsis. Plant Cell. 17: 3470-88. 2005.
Mitsuda N, Hiratsu K, Todaka D, Nakashima K, Yamaguchi-Shinozaki K, Ohme-Takagi M. Efficient production of male and female sterile plants by expression of a chimeric repressor in Arabidopsis and rice. Plant Biotech. J. 4: 325-32. 2006.
Mitsuda N, Iwase A, Yamamoto H, Yoshida M, Seki M, Shinozaki K, Ohme-Takagi M. NAC transcription factors, NST1 and NST3, are key regulators of the formation of secondary walls in woody tissues of Arabidopsis. Plant Cell. 19: 270-280. 2007.
Koyama T, Furutani M, Tasaka M, Ohme-Takagi M. TCP Transcription Factors Control the Morphology of Shoot Lateral Organs via Negative Regulation of the Expression of Boundary-Specific Genes in Arabidopsis. Plant Cell. 19: 473-484. 2007.
Ito T, Nagata N, Yoshiba Y, Ohme-Takagi M, Ma H, Shinozaki K. Arabidopsis Male STERILITY1 encodes a PHD-type transcription factor and regulates pollen and tapetum development. Plant Cell. 19: 3549-3562. 2007.
Groszmann M, Pacu T, Smyth DR. Functional domains of SPATULA, a bHLH transcription factor involved in carpel and fruit development in Arabidopsis. Plant J. 55: 40-52. 2008.
Matsuo N, Banno H. The Arabidopsis tranacription factor ESR1 induces in vitro shoot regeneration though transcriptional activation. Plant Physiol Biochem. 46: 1045-50. 2008.
Santos-Mendoza et al., Deciphering gene regulatory networks that control seed development and maturation in Arabidpsis, 54 Plant Journal, 608-620 (2008), published online Feb. 14, 2008.
Hiratsu et al., (Dominant repression of target genes by chimeric repressors that include the EAR motif, a repression domain, in Arabidopsis, 34 Plant Journal, 733-739 (2003).

* cited by examiner

A
Reporter
GAL4-LUC    CaMV35S'-5 X GAL4-TATA-[LUC]-NOS

Effector
GAL4DB      CaMV35S-Ω-[GAL4DB]-NOS
EAR         CaMV35S-Ω-[GAL4DB][EAR]-NOS
2g36080     CaMV35S-Ω-[GAL4DB][         ]NOS
(1/244)
1/169       CaMV35S-Ω-[GAL4DB][     ]-NOS
(2g36080-1stEX)
de178 to 192  CaMV35S-Ω-[GAL4DB][    ⋁   ]NOS
178/192     CaMV35S-Ω-[GAL4DB]-[ ]-NOS C
Reporter
GAL4-LUC    CaMV35S'-5 X GAL4-TATA-[LUC]-NOS Effector
GAL4DB           CaMV35S-Ω-[GAL4DB]-NOS
36RD (178/192)   CaMV35S-Ω-[GAL4DB]-[ ]-NOS
(GNSKTLRLFGVNMEC)
183/190          CaMV35S-Ω-[GAL4DB]-[ ]-NOS
(LRLFGVNM)

A

Reporter
GAL4-LUC    CaMV35S'-5 X GAL4-TATA-LUC-NOS

Effector
GAL4DB      CaMV35S-Ω-GAL4DB-NOS

At4g36990   CaMV35S-Ω-GAL4DB──────-NOS
(1/284)

233/243     CaMV35S-Ω-GAL4DB-□-NOS
                            GEGLKLFGVWL (SEQ ID NO:33)

mut 236 to 243   CaMV35S-Ω-GAL4DB─────■──-NOS
                            -- GEGAGAAGAWA--- (SEQ ID NO:71)

B

Bar= 0.5 cm

ID NO. 73), where X represents
TRANSCRIPTIONAL REPRESSOR PEPTIDES AND GENES FOR THE SAME

CROSS REFERENCE TO RELATED APPLICATIONS

The present application is a U.S. 371 National Stage Entry of pending International Patent Application No. PCT/JP2009/054718, International Filing Date Mar. 12, 2009, which claims the benefit of Japanese Patent Application No. 2008-062113, filed Mar. 12, 2008, both of which are hereby incorporated by reference in their entireties.

TECHNICAL FIELD

The present invention relates to (i) a peptide which is capable of repressing transcription, (ii) a gene encoding the peptide, (iii) a chimeric protein which is capable of repressing transcription, the chimeric protein including the peptide and a transcription factor or its DNA-binding domain, the peptide binding to the transcription factor or its DNA-binding domain, (iv) a chimeric gene encoding the chimeric protein, (v) a recombinant vector including the chimeric gene, and (vi) a transformant including recombinant the vector.

BACKGROUND ART

The antisense method and the ribozyme method are conventionally known as means of repressing expression of organisms' genes. These techniques have been studied so as to be applied to, e.g., repression of expression of disease-causing genes (such as oncogenes) or improvement of plants. The antisense method employs antisense DNA or RNA that is complementary to a specific site of a target gene, transcription of which is to be repressed, or mRNA to which the target gene has been transcribed. The prepared antisense DNA or RNA, however, cannot be used to repress expression of genes other than the target gene. Thus, for other genes, it is necessary to all the way prepare antisense DNA or RNA in accordance with sequences of the respective genes. In the case of the ribozyme method, in order to cleave target DNA or mRNA with a ribozyme, the ribozyme must be designed (i) to have a sequence complementary to the target DNA or mRNA so as to bind thereto and (ii) to cleave the target DNA or mRNA at a predetermined position. Even if the ribozyme is designed to cleave the target gene, the following problem may occur: For example, in a case where such the ribozyme is linked to a promoter (e.g., the cauliflower mosaic virus 35S promoter) and a transcription terminator sequence in order to construct a vector for introduction and the resulting vector is actually introduced to a plant cell, an excessive sequence is added to a transcribed ribozyme, which may result in loss of ribozyme activity. In addition, in these conventional techniques, identification of the target gene and determination of its nucleotide sequence are always indispensable. This has been a big problem, particularly when these techniques are used for improvement in plant traits. The reason for this is that most studies on plants have been conducted with use of model plants, and there is little finding on gene sequences of practical plants which are used as food, fuels, building materials, etc., and therefore it is very difficult to design appropriate antisense DNA or RNA or an appropriate ribozyme. Moreover, it is well known that the practical plants have big differences in their gene sequences between the types, or even between the individuals. In view of this, it is almost impossible to design appropriate antisense DNA or an appropriate ribozyme for each type of the practical plants. In addition to the above-described methods, as a technique for repressing expression of a target gene, there is a method for disrupting a target gene itself by a gene knock-out method, which disrupts an endogenous gene by a chemical treatment, radiation, or introduction of a foreign gene. However, this method is difficult to apply to, e.g., amphidiploid plants, which inherently have a large number of gene sets, since it is difficult to disrupt all of the genes of the amphidiploid plants by this method. Examples of polyploid plants encompass soybean and wheat, each of which is an important crop as food and animal feeding stuff. In plants, genes often redundantly exist for an important function. Thus, also in cases of general diploid plants, it is difficult to disrupt all genes by the gene knock-out method.

In order to address these problems, the present inventors have developed CRES-T (chimeric repressor silencing technology), which is a completely different approach from the above conventional techniques (see Patent Literatures 1 through 8 and Non-Patent Literatures 1 through 3). The CRES-T is a technique that uses a transcriptional repression domain (dominant repressor) isolated from a plant. Namely, according to the CRES-T, such the transcriptional repression domain is bound to the carboxyl terminus of a transcriptional activator so as to impart strong transcriptional repression activity to the transcriptional activator, and then a chimeric gene including nucleic acid molecules encoding the transcriptional repression domain and the transcriptional activator is expressed in a plant, so that transcription of a target gene is strongly repressed. Further, such the chimeric gene, to which the transcriptional repression domain has fused, represses not only the transcriptional activator but also functions of all other transcriptional activators that function redundantly with respect to the same gene. Therefore, plants produced by the CRES-T exhibit traits resulting from complete repression of expression of the target gene. Thus, the CRES-T is very useful not only for transformation of the practical plants but also for unravelment of basic functions of genes. Furthermore, the CRES-T can repress functions of a related gene whose sequence and functions are analogous to those of the target gene. Therefore, unlike the conventional antisense method and ribozyme method, the CRES-T does not need to design DNA or RNA according to a nucleotide sequence of each target gene. Thus, the CRES-T can be carried out in a simple manner, and is widely applicable.

The transcriptional repression domain consists of a motif (L/F)DLN(L/F)(X)P (SEQ ID NO. 73), where X represents any amino acid residue. At first, the transcriptional repression domain was isolated from *Arabidopsis thaliana*, and therefore the studies were conducted mainly on *Arabidopsis thaliana*. Afterward, the same motif as above was identified in transcriptional repressors of a wide variety of plants, examples of which include *Nicotiana tabacum* and monocotyledons such as *Oryza sativa*. So far, it has been demonstrated that, by converting a transcription factor functioning in the secondary metabolism biosynthesis system into a chimeric transcriptional repressor, it is possible to actively regulate the secondary metabolism biosynthesis. Further, the following experimental result has been obtained: By converting a transcription factor that regulates formation of floral organs into a chimeric transcriptional repressor and causing the chimeric transcriptional repressor to express in plants, male sterility and complete sterility were successfully induced with a high probability not only in *Arabidopsis thaliana* but also in *Oryza sativa*. These results show that the CRES-T is also applicable to *Oryza sativa*, which is a monocotyledon. Thus, the CRES-T attracts attention as a revolutionary technology that can be applied to a wide variety of general plants.

However, not only for plants but also for overall living organisms, the motif (L/F)DLN(L/F)(X)P (SEQ ID NO. 73) is the only conserved motif which has been found so far to be the transcriptional repression domain. After the finding of the motif (L/F)DLN(L/F)(X)P (SEQ ID NO. 73), the present inventors found that the motif "DLELRL" (SEQ ID NO. 74) is included in publicly-known SUP gene as a transcriptional repression function domain. However, no other transcribed gene has been found that includes the motif "DLELRL" (SEQ ID NO. 74), and therefore it cannot be said that this motif is a conserved motif. On this account, it has been demanded to find a conserved motif of a transcriptional repression domain like the motif (L/F)DLN(L/F)(X)P (SEQ ID NO. 73), i.e., a conserved motif that is applicable to general plants and conserved in natural transcriptional repressors.

[Patent Literature 1]
Japanese Patent No. 3829200
[Patent Literature 2]
Japanese Patent No. 3995211
[Patent Literature 3]
Japanese Patent Application Publication, Tokukai, No. 2001-269177 A
[Patent Literature 4]
Japanese Patent Application Publication, Tokukai, No. 2001-269178 A
[Patent Literature 5]
Japanese Patent Application Publication, Tokukai, No. 2001-292776 A
[Patent Literature 6]
Japanese Patent Application Publication, Tokukai, No. 2001-292777 A
[Patent Literature 7]
Japanese Patent Application Publication, Tokukai, No. 2001-269176 A
[Patent Literature 8]
Japanese Patent Application Publication, Tokukai, No. 2001-269179 A
[Non-Patent Literature 1]
The Plant Cell, 2001 13, 1959-1968
[Non-Patent Literature 2]
Plant Biotechnology J 2006. 4. 325-332
[Non-Patent Literature 3]
Plant Journal 2003 34:733-739.

SUMMARY OF INVENTION

Technical Problem

An object of the present invention is to provide a conserved motif sequence serving as a novel transcriptional repression domain available in the CRES-T, which is simple and widely applicable means for repressing transcription of genes, in order to broaden the range to which the CRES-T can be applied and to improve applicability of the CRES-T.

Solution to Problem

In order to attain this object, the present inventors focused on At2g36080 gene, which is a transcribed gene of *Arabidopsis thaliana*. The present inventors conducted a transient assay on *Arabidopsis thaliana* leaves with use of an effector construct prepared by fusing a GAL4 DNA-binding domain to At2g36080 gene. As a result, the present inventors found that the effector construct has strong transcriptional repression activity, and also found that the region having the transcriptional repression activity was eight peptides "LRLFGVNM" (SEQ ID NO. 32). Next, from all genes registered in the *Arabidopsis thaliana* database, the present inventors found 29 transcriptional regulator genes each including an amino acid sequence analogous to the motif LRLFGVNM (SEQ ID NO. 32). Among these, At3g11580, At2g46870, At1g13260, At1g68840, At4g36990, and At4g11660 were subjected to the same transient assay as above. As a result, all of these genes were proved to function as transcriptional repressors. Of the transcriptional repressors, six genes had RLFGV (SEQ ID NO. 75) as a conserved sequence, whereas At4g36990 had KLFGV (SEQ ID NO. 76) as a conserved sequence. At4g36990 was analyzed by using an effector plasmid into which further mutation had been introduced. As a result, five amino acids "K/RLFGV" (SEQ ID NO. 77) (first one amino acid is K or R) were determined as a conserved sequence. Meanwhile, the following experiment was carried out: DNA fragments each encoding 15 amino acids, which were a partial fragment of an amino acid sequence encoded by At2g36080 gene and which included RLFGV, were fused to CUC2 gene and AG gene (both of which are transcriptional activators derived from *Arabidopsis thaliana*), respectively, so as to prepare constructs. Then, these constructs were introduced into *Arabidopsis thaliana*. As a result, it was found that fused cotyledons and double flower had been induced therein, as with a case involving use of a publicly-known transcriptional repression domain SRDX (LDLELRLGFA) (SEQ ID NO. 72). Thus, the present invention was completed.

Specifically, the present inventors fused the yeast-derived GAL4 DNA-binding domain to a gene (accession number At2g36080, classified as a transcribed gene in the *Arabidopsis thaliana* database), so as to obtain a chimeric gene serving as an effector construct that expressed under control of the CaMV 35S promoter (35S:GAL4DBAt2g36080, see A of FIG. 1). Then, the effector construct thus obtained was introduced into *Arabidopsis thaliana* leaves together with a reporter gene including (i) the enhancer region of CaMV 35S and (ii) the GAL4 DNA-binding region (35S-GAL4-TATA-LUC, see A of FIG. 1), and was caused to transiently express therein (transient assay). Consequently, activity of the reporter gene was remarkably repressed, compared with a control (pUC18 or 35S:GAL4DB, see A of FIG. 1). This suggests that At2g36080 gene functions as a transcriptional repressor (see B of FIG. 1).

In order to identify the transcriptional repression domain of At2g36080, transient assays were conducted as follows: The coding regions of At2g36080 genes were cut from their respective carboxyl terminuses, and effector constructs including At2g36080 genes having different lengths of coding regions were prepared (see A of FIG. 1). Then, transient assays were conducted with use of these effector constructs, with the result that the amino acid region 178-192 (15-amino acid region) was found to include a region having strong transcriptional repression activity (see B of FIG. 1). Further, only this region was cut out and fused with the GAL4 DNA-binding domain, so that an effector construct was prepared (see A of FIG. 1). The effector construct thus prepared also exhibited strong transcriptional repression activity (see B of FIG. 1). Thus, this region was found to serve as the transcriptional repression domain (repression domain) which imparts transcriptional repression activity to a DNA-binding domain.

The peptide consisting of these 15 amino acids was subjected to a further detailed analysis. As a result, even only with eight amino acids LRLFGVNM (SEQ ID NO. 32) (the amino acids 183-190), the peptide was found to function as the repression domain (see C and D of FIG. 1).

Next, in all genes registered in the *Arabidopsis thaliana* database, the present inventors searched for genes having a sequence analogous to LRLFGVNM (SEQ ID NO. 32). Consequently, the present inventors found out genes encoding 29 transcriptional regulators, respectively (see Table 1, List of [RK]LFGV) (SEQ ID NO. 77). Of these genes, seven genes, At2g36080, At3g11580, At2g46870, At1g13260, At1g68840, At4g36990, and At4g11660, were subjected to the same transient assay as above, with the result that all of the seven genes were proved to be transcriptional repressors (see A through G of FIG. 2). Next, At2g36080, which had been originally used for identifying the transcriptional repression domain, was in detail compared with the six genes which were additionally identified as the transcriptional repressors, in terms of their amino acid sequences. Consequently, five amino acids K/RLFGV (SEQ ID NO. 77) (first one amino acid is K or R) were found to be a conserved sequence (see List of [RK]LFGV) (SEQ ID NO. 77). Of these, six genes had RLFGV (SEQ ID NO. 75) as a conserved sequence, whereas At4g36990 (see F of FIG. 2) had KLFGV (SEQ ID NO. 76) as a conserved sequence. Therefore, for At4g36990, a further detailed analysis was conducted on the domain of interest with use of, e.g., an effector plasmid into which mutation had been introduced. As a result, an 11-amino acid region including KLFGV (SEQ ID NO. 76) (GEGLKLFGVWL (SEQ ID NO. 33), the amino acids between 233 and 243) was found to have transcriptional repression activity (see A and B of FIG. 3). From these, all of the transcription factor genes (see Table 1), which have been found to include K/RLFGV (SEQ ID NO. 77) as a result of the search in the database, are assumed to function as transcriptional repressors in plants.

TABLE 1

List of *Arabidopsis thaliana*-derived transcription factors including [RK]LFGV (SEQ ID NO. 77)

| Locus | Gene name | Family name | Sequence | Position | Rice Homologue | SEQ ID No. |
|---|---|---|---|---|---|---|
| At2g36080.1 | | ABI3/VP1 | GNSKTLRLFGVNMEC | −57 | yes | 3 |
| At3g11580.1 | | ABI3/VP1 | GSSRTVRLFGVNLEC | −50 | | 4 |
| At5g06250 | | ABI3/VP1 | GSSRTVRLFGVNLEC | −49 | yes | 5 |
| At2g46870 | | ABI3/VP1 | TAGKRLRLFGVDMEC | −66 | yes | 6 |
| At1g01030 | | ABI3/VP1 | TAGKRLRLFGVNMEC | −70 | yes | 7 |
| At3g61970 | | ABI3/VP1 | RGEKRLRLFGVDMEC | −80 | yes | 8 |
| At4g01500 | | ABI3/VP1 | STTKKLRLFGVDVEE | −68 | yes | 9 |
| At1g13260 | RAV1 | AP2/ERF | DAGRVLRLFGVNISP | −38 | | 10 |
| At1g68840 | RAV2 | AP2/ERF | PVQVVVRLFGVDIFN | −44 | yes | 11 |
| At3g25730 | | AP2/ERF | ETGRVMRLFGVDISL | −30 | | 12 |
| At1g25560 | | AP2/ERF | PVQTVVRLFGVNIFN | −44 | | 13 |
| At1g35240 | | ARF | KAVTNFRLFGVSLAI | −145 | | 14 |
| At1g34310 | | ARF | KTGTNFRLFGVTLDT | −132 | | 15 |
| At1g34390 | | ARF | KTGTNFRLFGVSLVT | −139 | | 16 |
| At1g34410 | | ARF | KAGTNFRLFGVTLDT | −145 | | 17 |
| At1g35520 | | ARF | KAGTNFRLFGVSLAT | −132 | | 18 |
| At1g35540 | | ARF | NAVASFRLFGVSLAT | −145 | | 19 |
| At4g36990 | AT-HSFB1 | HSF | GVGEGLKLFGVWLKG | −44 | yes | 20 |
| At5g62020 | AT-HSFB2A | HSF | EEEASPRLFGVPIGL | −44 | | 21 |
| At4g11660 | AT-HSFB2B | HSF | GEDLTPRLFGVSIGV | −60 | yes | 22 |
| At2g41690 | AT-HSFB3 | HSF | EEDEGLKLFGVKLE | −4 | | 23 |
| At1g46264 | AT-HSFB4 | HSF | SNMRKTKLFGVSLPS | −39 | yes | 24 |
| At3g16350 | | MYB | GSSSAVKLFGVRLTD | −336 | yes | 25 |
| At5g47390 | | MYB | CPNRGVKLFGVRLTE | −338 | yes | 26 |
| At5g56840 | | MYB | YQTRVVRLFGVHLDT | −203 | yes | 27 |
| At5g61620 | | MYB | VNKASVKLFGVNISS | −279 | | 28 |
| At1g30810 | | JUMONJI | ASLTKGKLFGVDLM | −4 | | 29 |
| At2g34880 | | JUMONJI | QSLSKARLFGVDLN | −4 | | 30 |
| At2g37650 | | GRAS | RLAAYAKLFGVPFE | −205 | | 31 |

Next, the present inventors conducted analyses so as to determine (i) whether or not it is possible to functionally convert activity of a transcriptional activator, which inherently has ability of transcriptional activation, into a transcriptional repressor, by fusing the transcriptional regulator with the above-identified transcriptional repressor peptide [K/R] LFGV (SEQ ID NO. 77); and (ii) whether or not a chimeric gene encoding such the chimeric protein actually functions as a transcriptional repressor in a plant and induces a change of a trait of the plant. Model genes of a transcriptional activator used in actual experiments were *Arabidopsis thaliana*-derived CUC2 gene and AG gene. Note that CUC2 gene and AG gene have already been proved to be related to changes of traits of plants, by experiment using a publicly-known transcriptional repressor peptide (see Non-Patent Literatures 2 and 3).

With regard to the transcriptional repression domain SRDX (LDLELRLGFA) (SEQ ID NO. 72) that has already been reported by the present inventors, the following fact is known: In a case where (i) a chimeric gene (35S: CUC2SRDX) produced via fusion to the C-terminus of CUC2 gene or (ii) a chimeric gene (35S:AGSRDX) produced via fusion to the C-terminus of AG gene (see Non-Patent Literature 2) is expressed in *Arabidopsis thaliana*, fused cotyledons are induced in a 35S:CUC2SRDX plant (see D of FIG. 4), whereas a double flower is induced in a 35S:AGSRDX plant (see B of FIG. 4). In view of this, the 15 amino acids including RLFGV (SEQ ID NO. 75) (indicated as "36RD" in FIG. 4), i.e., a novel repression domain found by the present invention, were fused to the C-terminus of each of CUC2 gene and AG gene. Thus, chimeric genes (35S:CUC2-36RD and 35S:AG-36RD) were prepared (see A of FIG. 4). Then, analyses were conducted to determine if *Arabidopsis thaliana* into which these chimeric genes were introduced showed similar traits to those explained above.

As a result, fused cotyledons were induced in the plant into which 35S:CUC2-36RD (see E of FIG. 4) was introduced, as well as in 35S:CUC2-SRDX; and a double flower was induced in the plant into which 35S:AG-36RD (see C of FIG. 4) was introduced, as well as in 35S:AG-SRDX. This demonstrates that [RK]LFGV (SEQ ID NO. 77) peptide, which has been found by the present inventors, functions in plants, as well as SRDX does. Further, the trait of the double flower observed in 35S:AG-36RD closely resembled the trait observed in the plant in which AG gene was disrupted (ag mutant). From this, this trait was considered to be induced as follows: The 36RD which was fused to the AG gene induced functional conversion of AG gene. Accordingly, 35S:AG-36RD chimeric gene, which became a strong transcriptional repressor, functioned to repress expression of all target genes whose transcription was to be activated by AG. This trait clearly shows that 35S:AG-36RD chimeric gene functions dominantly over endogenous AG gene. Note that the fused cotyledons observed in 35S:CUC2-36RD are the trait (cuc1 cuc2) observed only when two genes, CUC2 gene and CUC1 gene (analogous gene that functions in a complementary manner with CUC2), are disrupted. According to this fact, 35S:CUC2-36RD chimeric gene is proved to function dominantly over not only endogenous CUC2 gene but also CUC1 gene, which has the same function as that of CUC2 gene, so as to repress expression of the target genes.

The present invention encompasses the following aspects:

[1] A peptide which is capable of repressing transcription in a plant, including an amino acid sequence represented by the following formula (I):

```
X1-X2-Leu-Phe-Gly-Val-X3,    (SEQ ID NO: 78)
``` where each of X1 and X3 independently represents an amino acid sequence consisting of any 1 to 10 amino acids, and X2 represents Lys or Arg.

[2] The peptide of [1], wherein:
the amino acid sequence included in the peptide is shown in one of SEQ ID NO: 3 to 33.

[3] Nucleic acid molecules encoding the peptide of [1] or [2].

[4] A chimeric protein which is capable of repressing transcription, including:
a peptide which is capable of repressing transcription in a plant; and
a transcription factor or its DNA-binding domain,
the peptide binding to the transcription factor or its DNA-binding domain, and the peptide including an amino acid sequence represented by the following formula (I):

```
X1-X2-Leu-Phe-Gly-Val-X3,    (SEQ ID NO: 78)
``` where each of X1 and X3 independently represents an amino acid sequence consisting of any 1 to 10 amino acids, and X2 represents Lys or Arg.

[5] Nucleic acid molecules encoding a chimeric protein which is capable of repressing transcription, including:
first nucleic acid molecules encoding a peptide which is capable of repressing transcription in a plant; and
second nucleic acid molecules encoding a transcription factor or its DNA-binding domain,
the first nucleic acid molecules being linked in frame with the second nucleic acid molecules, and
the peptide encoded by the first nucleic acid molecules including an amino acid sequence represented by the following formula (I):

```
X1-X2-Leu-Phe-Gly-Val-X3,    (SEQ ID NO: 78)
``` where each of X1 and X3 independently represents an amino acid sequence consisting of any 1 to 10 amino acids, and X2 represents Lys or Arg.

[6] An expression vector including nucleic acid molecules of [5].

[7] A transformant into which nucleic acid molecules of [5] have been introduced in a manner that allows the nucleic acid molecules to be expressed therein.

[8] A transformed plant into which nucleic acid molecules of [5] have been introduced in a manner that allows the nucleic acid molecules to be expressed therein.

[9] A method for producing a chimeric protein which is capable of repressing transcription, including the steps of:
transforming cells with use of an expression vector including nucleic acid molecules of [5];
culturing the cells thus transformed, in order to obtain an expression product;
collecting the expression product; and
purifying the expression product.

[10] A method for producing a chimeric protein which is capable of repressing transcription, including the step of:
linking (i) a peptide which is capable of repressing transcription in a plant to (ii) a transcription factor or its DNA-binding domain,
the peptide including an amino acid sequence represented by the following formula (I):

```
X1-X2-Leu-Phe-Gly-Val-X3,    (SEQ ID NO: 78)
``` where each of X1 and X3 independently represents an amino acid sequence consisting of any 1 to 10 amino acids, and X2 represents Lys or Arg.

Advantageous Effects of Invention

As well as conventionally-known peptides capable of repressing transcription, the peptide of the present invention, having a very short length, is capable of effectively repressing transcription of a gene. Further, the chimeric protein bound to (i) a transcription factor that binds to a transcriptional regulatory domain of a specific target gene or (ii) its DNA-binding domain has ability to convert the transcription factor into a transcriptional repressor.

Therefore, as well as genes encoding the publicly-known peptides capable of repressing transcription, the gene of the present invention, obtained as a chimeric gene produced via fusion with (i) a gene encoding a transcription factor that binds to a transcriptional regulatory domain of a specific target gene or its DNA-binding domain or (ii) a gene which forms a transcriptional regulatory complex with the transcriptional regulator, is capable of repressing transcription of only a specific gene, and also is capable of repressing functions of other transcription factors that redundantly involve transcription to be activated by the transcription factor included in the chimeric gene. Thus, the gene of the present invention can reliably inhibit transcription and expression of the target gene.

Furthermore, the peptide of the present invention has a conserved motif which is completely different from those of the publicly-known peptides capable of repressing transcription. Therefore, use of the peptide of the present invention instead of or in combination with any of the publicly-known peptides will further broaden an application range in breeding of various plants.

BRIEF DESCRIPTION OF DRAWINGS

In FIG. 1, A is a view illustrating (i) GAL4DB-RD effector plasmids including various DNA fragments to be tested and (ii) a reporter gene, each of which was used to determine a domain having transcriptional repression activity in At2g36080 gene. Note that "5XGAL4" represents a DNA binding sequence of GAL4 transcription factor; "TATA" represents a region including the TATA box of the CaMV35S promoter; "LUC" represents a luciferase gene; "CaMV35S" represents the cauliflower mosaic virus 35S protein gene promoter; "Ω" represents an omega sequence derived from the tobacco mosaic virus; "GAL4DB" represents a region encoding the DNA-binding domain of the yeast GAL4 transcription factor; "RD" represents the sequence of a repression domain (LDLELRLGFA) of SUPERMAN; and "Nos" represents the transcription termination region of nopalin synthase gene.

In FIG. 1, B is a view illustrating effects on activity (relative activity) of the reporter gene, which effects were given by various peptides each bound to pGAL4DB.

The graph on the right shows activity of the reporter gene observed when the reporter gene and each of the effector plasmids including various DNA fragments were introduced into Arabidopsis thaliana leaves (activity of the reported gene observed in a case where PUC18 was introduced as an effector was defined as 1.00).

Figure 1:
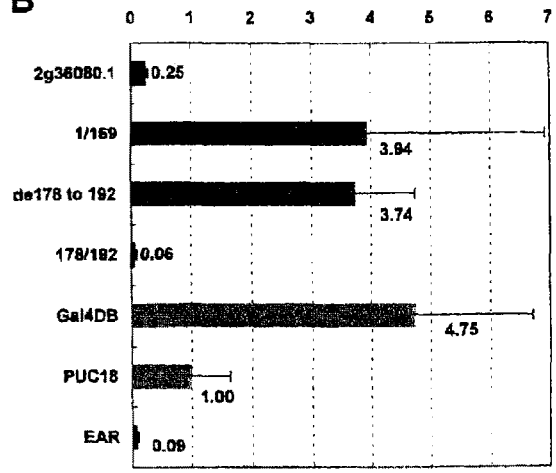
FIG. 1
Figure 1:
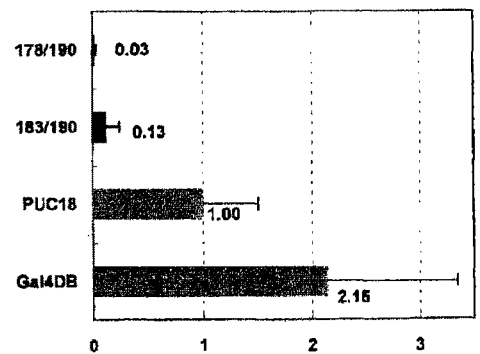

In FIG. 1, C is a view illustrating a reporter gene and effector plasmids, each of which was used to determine a domain having transcriptional repression activity in At2g36080 gene.

In FIG. 1, D is a view illustrating effects on activity (relative activity) of the reporter gene, which effects were given by various peptides each bound to pGAL4DB. In D of FIG. 1, the graph on the right shows activity of the reporter gene observed when the reporter gene and each of the effector plasmids including various DNA fragments were introduced into Arabidopsis thaliana leaves (activity of the reported gene observed when PUC18 was introduced as an effector was defined as 1.00).

FIG. 2

Figure 2:
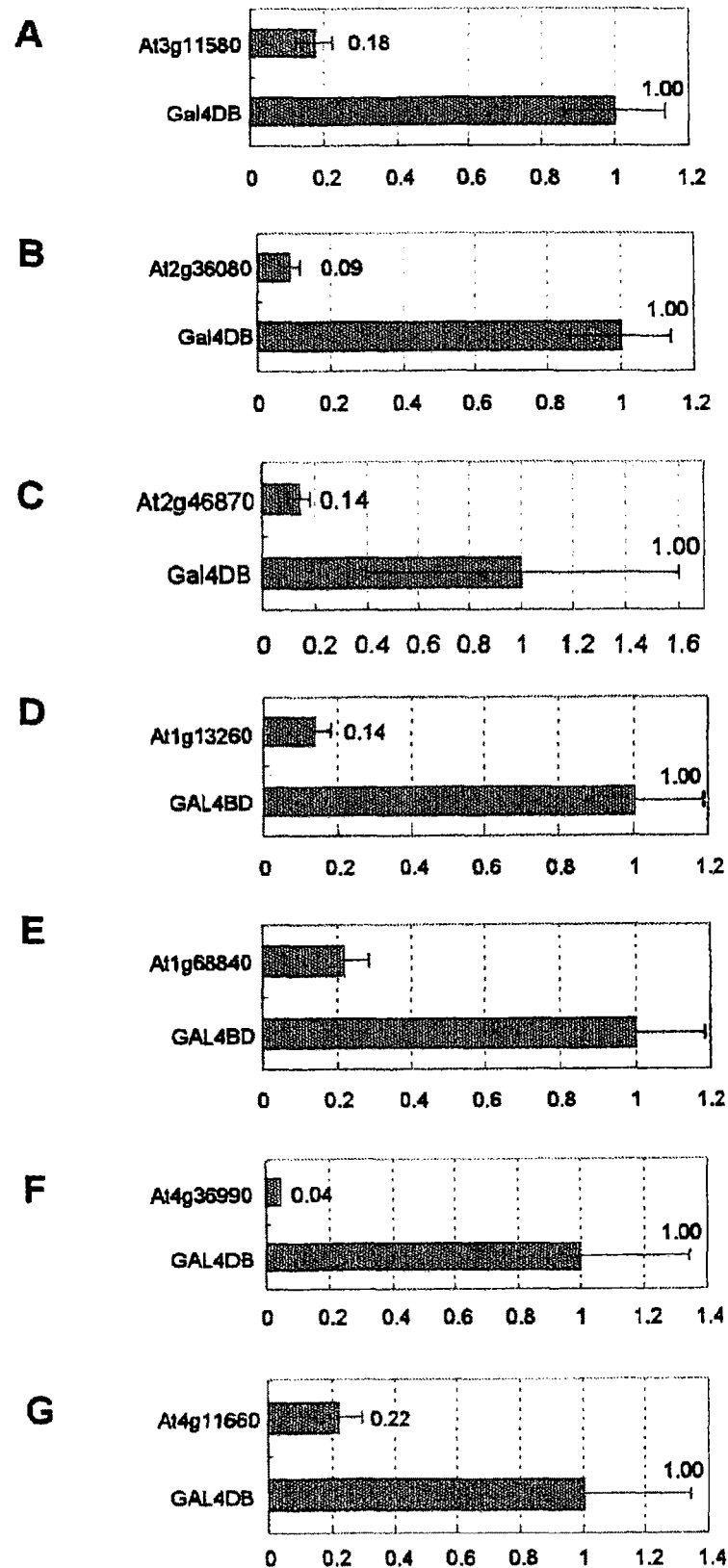

FIG. 2 is a view illustrating effects on activity (relative activity) of the reporter gene, which effects were given by various genes each bound to pGAL4DB. In FIG. 2, the graph on the right shows activity of the reporter gene observed when the reporter gene and each of the effector plasmids including various DNA fragments were introduced into Arabidopsis thaliana leaves (activity of the reported gene observed when pGAL4DB was introduced as an effector was defined as 1.00).

In FIG. 2, A shows activity of the reporter gene observed when At3g11580 gene was introduced; B shows activity of the reporter gene observed when At2g36080 gene was introduced; C shows activity of the reporter gene observed when At2g46870 gene was introduced; D shows activity of the reporter gene observed when At1g13260 gene was introduced; E shows activity of the reporter gene observed when At1g68840 gene was introduced; F shows activity of the reporter gene observed when At4g36990 gene was introduced; and G shows activity of the reporter gene observed when At4g11660 gene was introduced.

FIG. 3

Figure 3:
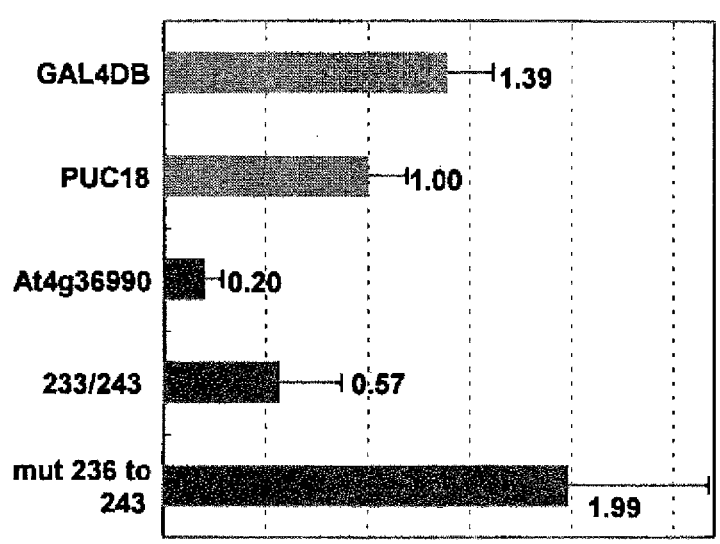

In FIG. 3, A is a view illustrating a reporter gene and effector plasmids, each of which was used to determine a domain having transcriptional repression activity in At4g36990 gene.

In FIG. 3, B is a view illustrating effects on activity (relative activity) of the reporter gene, which effects were given by various peptides each bound to pGAL4DB. In FIG. 3, the graph on the right shows activity of the reporter gene observed when the reporter gene and each of the effector plasmids including various DNA fragments were introduced into Arabidopsis thaliana leaves (activity of the reported gene observed when PUC18 was introduced as an effector was defined as 1.00).

FIG. 4

Figure 4:
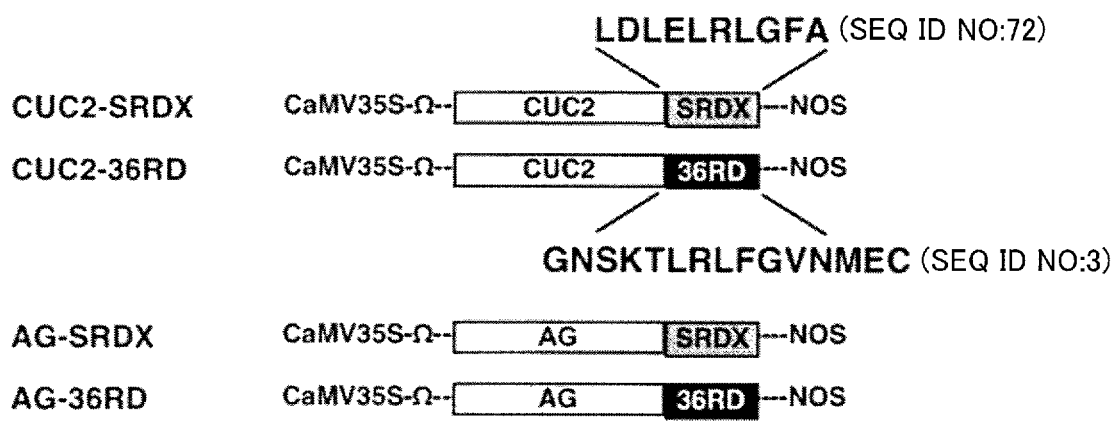
Figure 4:
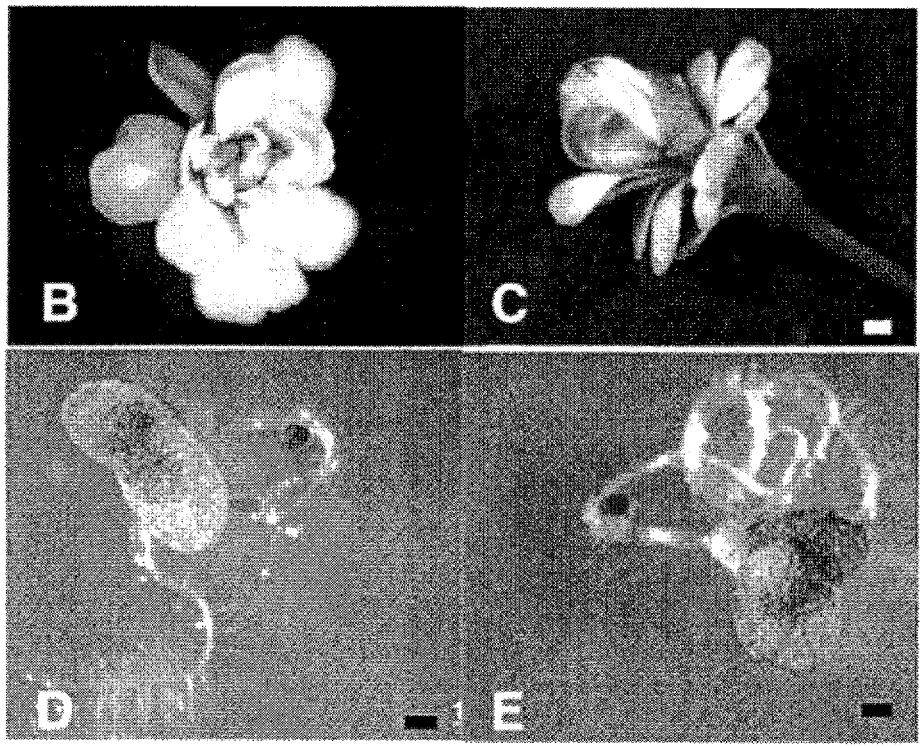

In FIG. 4, A is a view schematically illustrating constructs prepared by fusing various genes with transcriptional repressor peptides, which constructs were introduced into plants.

In FIG. 4, B shows the morphology of the flower of AG-SRDX.

In FIG. 4, C shows the morphology of the flower of AG-36RD.

In FIG. 4, D shows the morphology of the seedling of CUC2-SRDX.

In FIG. 4, E shows the morphology of the seedling of CUC2-36RD.

DESCRIPTION OF EMBODIMENTS

The following will describe the present invention in greater detail.

The present invention provides a peptide which is a transcriptional repressor including an amino acid sequence represented by the formula (I), and which has ability to convert a transcription factor into a transcriptional repressor. The formula (I) is as follows:

```
X1-X2-Leu-Phe-Gly-Val-X3,    (SEQ ID NO: 78)
``` where X2 represents Lys or Arg, each of X1 and X3 may be any amino acid(s), and an amino acid sequence represented by each of X1 and X3 may consist of any number of amino acids as long as the number of the amino acids is within a range from 1 to 10. Each of the amino acid sequences represented by X1 and X3 is preferably short, since this facilitates synthesis of the peptides to be used. However, in order to reliably enhance the repression effect, a total number of amino acids included in the amino acid sequences represented by X1 and X3 is preferably 3 or greater, more preferably 6 or greater, further preferably 10 or greater.

Preferable examples of the peptide of the present invention encompass the amino acid sequences shown in SEQ ID NO: 3 to 33, each of which amino acid sequences consists of 8 to 15 amino acids. The peptide of the present invention may be a peptide including an amino acid sequence with deletion, substitution, or addition of one or several amino acids in part of one of the amino acid sequences shown in SEQ ID NO: 3 to 33, which part corresponds to X1 or X3. Note that the expression "one or several" herein means 1 to 10, preferably 1 to 7, more preferably 1 to 5, further preferably 1 to 3.

The conserved motif included in the transcriptional repressor peptide of the present invention is "K/RLFGV" (SEQ ID NO. 77). The motif "K/RLFGV" (SEQ ID NO. 77) has an amino acid sequence different from that of the motif (L/F) DLN(L/F)(X)P (SEQ ID NO. 73), which is shown by the above-described conventional technique. Further, the motif "K/RLFGV" (SEQ ID NO. 77) is also completely different from the motif "DLELRL" (SEQ ID NO. 74) included in the amino acid sequence encoded by SUP gene, which motif has been found by the present inventors to be capable of repressing transcription.

These transcriptional repressor peptides, each of which is short, are easy to produce through chemical synthesis. Instead of the chemical synthesis, however, each of these transcriptional repressor peptides can be produced by cells transformed with use of a vector that is prepared by linking, to a suitable expression vector, the nucleic acid molecules encoding the peptide. In order for each of the transcriptional repressor peptides to function as a transcriptional repressor within a plant, a plant cell, or a yeast cell, the nucleic acid molecules encoding the transcriptional repressor peptide may be introduced into the cell either with or without being linked to an expression vector. Thus, the transcriptional repressor peptide can exhibit the transcriptional repression activity within the cell.

The preset invention also provides a chimeric protein which is capable of repressing transcription and which includes any of these transcriptional repressor peptides bound to a transcription factor or its DNA-binding domain.

The chimeric protein can be obtained through chemical bonding between (i) the transcriptional repressor peptide and (ii) the transcription factor or its binding domain. Typically, however, the chimeric gene is produced as follows: A chimeric gene is produced by causing (i) the nucleic acid molecules encoding the transcriptional repressor peptide of the present invention to be linked in frame with (ii) the nucleic acid molecules encoding the transcription factor or its DNA-binding. Then, under control of a suitable promoter, the chimeric gene thus produced is expressed in a cell that includes a target gene, so that the chimeric gene acts on the target gene. Specifically, the chimeric gene is linked to a promoter sequence, and a plant, a plant cell, or the like is transformed with or without an expression vector, so that the chimeric gene is expressed in the transformed cell and a chimeric protein is produced as an expression product. Also in this chimeric protein, the DNA-binding domain derived from the transcription factor binds to the transcriptional regulatory domain of the target gene. However, the transcriptional repression activity of the transcriptional repressor peptide acts dominantly over the transcriptional activation activity that the transcription factor originally has. Thus, transcription of the target gene is repressed, and therefore the target gene is not expressed.

The transcriptional repression activity of the chimeric protein of the present invention acts regardless of the type of the DNA-binding domain of the transcriptional regulator. In order that the chimeric protein of the present invention exerts the transcription repression activity, the chimeric protein should bind to a transcriptional regulatory domain of a target gene. Therefore, the gene encoding the chimeric protein is obtained as a chimeric gene produced via fusion with (i) a transcriptional regulator gene including a DNA-binding domain that binds to a transcriptional regulatory domain of a specific target gene, (ii) a nucleic acid sequence encoding the DNA-binding domain of the transcriptional regulator gene, or (iii) a gene which forms a transcriptional regulatory complex with a transcription factor that binds to the transcriptional regulatory domain of the specific target gene. With this, it is possible to repress transcription of only the specific gene.

Namely, the chimeric gene of the present invention expresses a chimeric protein in which (i) a peptide having ability to convert a transcription factor into a transcriptional repressor binds to (ii) a transcription factor. Further, the chimeric gene of the present invention specifically represses transcription of a gene, transcription of which is controlled by the transcriptional regulatory domain to which the DNA-binding domain derived from the transcription factor in the chimeric protein binds. Therefore, transcription of a specific gene can be repressed in the following manner: A transcription factor that regulates transcription of the specific gene is selected. Then, the gene of the present invention is linked to a terminus or a DNA-binding domain of a gene encoding the transcription factor, so as to construct a chimeric gene. The chimeric gene thus constructed is linked to a suitable vector, which is then introduced into a site of an organism where transcription of the specific gene is to be repressed. Thus, transcription of the specific gene is repressed.

Further, the chimeric protein, which is an expression product of the chimeric gene of the present invention, specifically represses transcription of a gene to which the DNA-binding domain of the transcription factor in the chimeric protein binds. The transcription repression acts as a dominant trait.

The same method as that used in Patent Literatures 1 through 8 and Non-Patent Literatures 1 through 3, i.e., the CRES-T, was employed so as to demonstrate the following fact: By fusing a transcriptional repressor peptide of the present invention to a transcriptional activator and expressing the resulting chimeric protein, the transcriptional activator is functionally converted into a transcriptional repressor, and transcription of a target gene which is to be activated by the transcription factor is specifically and dominantly repressed.

This will be described in a greater detail with reference to an example where AGAMOUS (AG) transcription factor was used.

AGAMOUS is a transcriptional activator that regulates formation of floral organs of *Arabidopsis thaliana*. An ag mutant in which AG activity is eliminated is known to have a so-called double flower, which has a lot of petals. This is because that, in the ag mutant, stamens and pistils are replaced by petals, and a lot of petals are continuously formed since formation of floral organs is not terminated, which ultimately leads to a double flower. Here, transcriptional activator AG was fused with the gene encoding a peptide of the present invention including the motif "K/RLFGV" (SEQ ID NO. 77), and the resulting chimeric gene was expressed in *Arabidopsis thaliana*. As a result, a double flower was obtained, as with the case involving use of the publicly-known motif (L/F)DLN(L/F)(X)P (SEQ ID NO. 73) (Non-Patent Literature 2). This demonstrates that (i) AG gene, capable of activating transcription, was functionally converted into a transcriptional repressor via fusion with the transcriptional repressor peptide of the present invention, and (ii) the functionally-converted AG gene functioned dominantly over endogenous AG gene.

The above will be described in greater detail with reference to an example where CUP-SHAPEDCOTYLEDON1 (CUC2) transcription factor was used (Non-Patent Literature 3).

CUC2 is a transcription factor that regulates formation of the apical buds of seedlings together with CUC1. Note that CUC1 and CUC2 have the same NAC domain. It is known that, only in a case of a plant in which both of CUC1 and CUC2 genes have mutation, the cotyledon thereof forms a cup-like shape (cup-shaped cotyledon), and apical meristem is not formed therefor. In contrast, a plant in which only either one of CUC1 and CUC2 genes has mutation is normal. From these, CUC1 and CUC2 are known to be functionally redundant factors (Development, 126, 1563, 1999; Development, 128, 1127, 2000). In a case where a chimeric gene is prepared by binding (i) the gene encoding the peptide of the present invention to (ii) either one of the functionally redundant CUC1 and CUC2 transcription factor genes, for example, CUC2 gene, and the resulting chimeric gene is allowed to express in a plant, the expressed chimeric protein can suppress not only transcription activity of CUC2 transcription factor but also that of CUC1 transcription factor, which is functionally redundant with CUC2. Consequently, the chimeric gene can repress expression of genes regulated by CUC2 transcription factor. In this case, the cotyledon of the plant forms a cup-like shape (cup-shaped cotyledon), which is a trait of a CUC1/CUC2 double mutant, and apical meristem is not formed therefor. In Example 6 (described later), a chimeric gene was constructed by fusing CUC2 gene with a gene encoding a peptide of the present invention that includes the motif "K/RLFGV" (SEQ ID NO. 77), and *Arabidopsis thaliana* was transformed with the chimeric gene thus constructed. As a result, this example demonstrates that (i) *Arabidopsis thaliana* thus transformed exhibited the trait of a cup-like shape (cup-shaped cotyledon), which is a phenotype of a CUC1/CUC2 double deletion mutant, and (ii) apical meristem was not formed for *Arabidopsis thaliana* thus transformed, as with the case of an STM gene deletion variant. Note that STM gene regulates formation of apical meristem, and is regulated by CUC2 transcription factor. These results indicate that (i) CUC2 transcription factor, which is capable of activating transcription, was functionally converted into a transcriptional repressor via fusion with the peptide of the present invention and (ii) CUC2 transcription factor thus converted into the transcriptional repressor dominantly suppressed not only activity of CUC2 transcription factor but also activity of CUC1 transcription factor, which is functionally redundant with CUC2 transcription factor, and repressed expression of genes located downstream. These results are similar to the results obtained in cases involving use of a transcriptional repressor peptide including the publicly-known motif "(L/F)DLN(L/F)(X)P" (SEQ ID NO. 73) (Non-Patent Literature 3).

As understood from the above, the peptide of the present invention and a gene encoding the peptide are each capable of (i) converting any transcription factor into a transcriptional repressor and (ii) suppressing activities of other transcription factors which are functionally redundant with the transcription factor.

In many cases, as demonstrated with reference to CUC, plants each have a plurality of transcription factors which are functionally redundant with each other. Further, a transcriptional repressor which has been functionally converted by the present invention appears as a dominant trait (dominant). Therefore, the present invention enables functional analyses of transcription factors that have not been elucidated by conventional single gene knocking-out technique, and can be effectively applied to plants having amphidiploid genomes (e.g., wheat). In terms of these, the present invention is very useful.

As described previously, the chimeric gene of the present invention causes production of a chimeric protein corresponding to the chimeric gene, which chimeric protein binds to a transcriptional regulatory domain of a target gene, so as to repress transcription of the target gene. Therefore, the chimeric protein may be separately synthesized and may be directly introduced into a site of an organism where a target gene exists.

The chimeric protein may be synthesized by a general technique of genetic engineering. For example, the chimeric protein may be synthesized in large quantity by incorporating the chimeric gene into a suitable vector, transforming microorganisms with the resulting vector, and culturing the microorganisms thus transformed.

The site where the gene of the present invention is fused to a transcription factor is the downstream terminus of a region encoding the transcription factor or its DNA-binding domain. Inserting the gene encoding the peptide of the present invention into a gene encoding a transcription factor involves laborious operations such as cleavage of the gene encoding the transcription factor, linking the gene encoding the transcription factor to the gene of the present invention, and joining these genes. Therefore, it is convenient to simply bind the gene of the present invention to the downstream terminus of the protein coding region in the transcription factor. This is one of the advantages of the present invention.

The gene of the present invention may have any nucleotide sequence as long as it encodes a peptide including an amino acid sequence represented by the previously-described formula (I). The gene of the present invention may have a site where the gene is linked to a gene encoding a transcription factor. In a case where the amino acid reading frame of the gene of the present invention does not match the reading frame of the gene encoding the transcription factor, the gene of the present invention should be designed to have a reading frame matching that of interest. Thus, the gene of the present invention may have an additional nucleotide sequence for this purpose. A nucleotide sequence encoding the amino acid sequence represented by the formula (I) is, for example, as follows:

```
                                              (SEQ ID NO: 65)
5'-GGGAGGCAACTCGAAGACATTAAGACTGTTCGGAGTGAACA

TGGAGTGCTAA-3'.
```

In the present invention, transcription of a target gene may be repressed by directly introducing the above-described chimeric protein into an organism. However, in a case where breed improvement in plants is intended, for example, it is necessary to constantly repress transcription of a specific gene in order to repress expression of the gene. Therefore, in such a case, it is more effective to link a gene encoding this chimeric protein to a suitable vector and transform a plant or the like with the resulting recombinant vector. This operation enables the gene encoding the chimeric protein to be constantly expressed in the plant, whereby the resulting chimeric protein keeps repressing transcription of the target gene. Further, this operation enables to repress expression of the target gene also in later-generation plants (including plants produced by, e.g., breeding using transformed pollens or the like) derived from the transformed plant into which the gene encoding the chimeric protein has been introduced, as long as a chimeric protein corresponding to the introduced chimeric gene is produced therein.

EXAMPLES

The following will describe the present invention with reference to examples. However, the present invention is not particularly limited to these examples.

In Example 1, (i) effector plasmids were constructed; specifically, each of the effector plasmids was constructed by binding (a) one of various At2g36080 gene fragments linked with a region encoding the DNA-binding domain of the yeast GAL4 transcription factor to (b) a downstream region of the cauliflower mosaic virus 35S promoter, which functions in plant cells. Further, in Example 1, (ii) a reporter gene was constructed by linking, to the promoter region of a luciferase gene, (a) the enhancer region of the cauliflower mosaic virus 35S promoter, (b) the DNA binding sequence of GAL4 protein, and (c) the TATA region of the cauliflower mosaic virus 35S promoter. The reporter gene and each of these effector plasmids were concurrently introduced into *Arabidopsis thaliana* leaves by a particle gun. Then, activity of the luciferase gene (i.e., the reporter gene) was assayed in order to investigate transcriptional repression activity of the following genes: a gene encoding a protein consisting of the entire amino acid sequence encoded by At2g36080; and a gene encoding an At2g36080 partial protein including the region 178-192 of the amino acid sequence encoded by At2g36080.

In Example 2, luciferase activity of the reporter gene was assayed in order to investigate transcriptional repression activity of a gene encoding an At2g36080 partial protein including the region 183-192 of the amino acid sequence encoded by At2g36080.

In Example 3, luciferase activity of the reporter gene was assayed in order to investigate transcriptional repression activity of genes respectively encoding proteins of At3g11580 gene, At2g46870 gene, At1g13260 gene, At1g68840 gene, At4g36990 gene, and At4g11660 gene, each of which proteins included the amino acid sequence R/KLFGV (SEQ ID NO: 77).

In Example 4, luciferase activity of the reporter gene was assayed in order to investigate transcriptional repression activity of a gene encoding an At4g36990 partial protein including the amino acids 233-243 of the amino acid sequence encoded by At4g36990.

In Example 5, AG gene, which is a transcription factor in an actual plant, was fused with a gene fragment encoding GNSKLTLRLFGVNMEC (SEQ ID NO: 3) (the repression domain 178-192 of 36RD;At2g36080), and the resultant was linked to a downstream region of the cauliflower mosaic virus 35S promoter, so as to construct a plasmid for transformation. Thereafter, the plasmid thus constructed was introduced into *Arabidopsis thaliana*, and the morphology of the flower of the transformed plant was observed. In this manner, effects of the above gene fragment in repressing transcription of a target gene of AG gene were investigated.

In Example 6, CUC2 gene, which is a transcription factor in an actual plant, was fused with a gene fragment encoding GNSKLTLRLFGVNMEC (SEQ ID NO: 3) (a repression domain 178-192 of 36RD;At2g36080), and the resultant was linked to a downstream region of the cauliflower mosaic virus 35S promoter, so that a plasmid for transformation was constructed. Thereafter, the plasmid thus obtained was introduced into *Arabidopsis thaliana*, and the morphology of the cotyledon of the transformed plant after germination was observed. In this manner, effects of the above gene fragment in repressing transcription of a target gene of CUC2 gene and CUC1 gene (which is functionally redundant with CUC2 gene) were investigated.

Example 1

Transcriptional Repression by Effector Plasmid Including At2g36080 Gene (1-1) Construction of Vector p35S-GAL4DBD for Effector Plasmid Plasmid pBI221 (available from Clontech, the U.S.A.) was cleaved with restriction enzymes XhoI and SacI, and was then blunt-ended with T4 polymerase. Thereafter, GUS gene was removed therefrom through agarose gel electrophoresis, so as to obtain a 35S-Nos plasmid DNA fragment including the cauliflower mosaic virus 35S promoter (hereafter referred to as "CaMV 35S") and the transcription termination region of a nopaline synthase gene (Nos terminator, hereafter referred to as "Nos-ter").

Next, pAS2-1 vector (available from Clontech) was digested with restriction enzyme HindIII, and a 748-bp DNA fragment encoding the DNA-binding domain (the amino acid residues 1-147) of the yeast GAL4 protein (hereafter referred to as "GAL4DBD") was isolated therefrom through agarose gel electrophoresis. Then, the DNA fragment thus isolated was blunt-ended with T4 DNA polymerase. The DNA fragment including the GAL4DBD-coding region was inserted into the blunt-ended site between the 35S promoter and the Nos terminator in the 35S-Nos DNA fragment. Then, the one in which the ORF of the DNA-binding domain of the yeast GAL4 protein was in the forward direction with respect to the 35S promoter was selected. Thus, p35S-GAL4DBD vector was constructed.

(1-2) Construction of Effector Plasmid (A of FIG. 1)

(1-2-1) Construction of Effector Plasmid pGAL4-At2g36080 Including Entire Protein-Coding Region (1-244aa.) of At2g36080 Gene Oligonucleotides were synthesized so as to include sequences corresponding to the sequences on the respective 5'- and 3'-ends of the protein-coding region of At2g36080 gene of *Arabidopsis thaliana*, whose nucleotide sequence has already been reported. One of the oligonucleotides included a sequence corresponding to a 5'-upper primer 1 of At2g36080 gene (that binds to the 1-29 region in the nucleotide sequence of At2g36080 gene):

gATGTCAATAAACCAATACTCAAGCGATTT. (SEQ ID NO: 34)

Note that the 5'-upper primer 1 was designed so as to be in frame with GAL4DBD. The other of the oligonucleotides included a sequence corresponding to a 3'-lower primer 1 of At2g36080 gene (that binds to the region 710-735 in the nucleotide sequence of At2g36080 gene): gtcgacgtcgacT-TAGCTCGTCCGGTTCATATCTCCT (SEQ ID NO: 35). Note that the 3'-lower primer 1 contained a SalI restriction site. PCR was carried out where (i) these oligonucleotides were used as primers and (ii) cDNA derived from the seedling of Arabidopsis thaliana was used as a template, and a DNA fragment including the protein-coding region of At2g36080 gene was isolated. This DNA fragment was digested with restriction enzyme SalI, and a DNA fragment of interest was isolated therefrom through agarose gel electrophoresis. Then, the DNA fragment thus isolated was incorporated into 35S-GAL4DBD plasmid which had already been digested with restriction enzymes SmaI and SalI. Thereafter, the nucleotide sequence of the insert was determined. As a result, the insert was confirmed to be the already-reported protein-coding region of At2g36080 gene.

Note that the PCR was carried out under the following conditions: 30 cycles each consisting of denaturation at 94° C. for one minute; annealing at 50° C. for one minute; and elongation at 72° C. for three minutes.

(1-2-2) Construction of Effector Plasmid pGAL4-At2g36080-1stEX Including Nucleotide Sequence Encoding Region 1-169 of Amino Acid Sequence Encoded by At2g36080 Gene Oligonucleotides were synthesized so as to include sequences corresponding to (i) a 5'-upper primer 1 of At2g36080 gene: gATGTCAATAAACCAATACTCAAGC-GATTT (SEQ ID NO: 34), and (ii) a lower primer 2 of At2g36080 gene (that binds to the region 491-506 in the nucleotide sequence of At2g36080 gene): AATAAAAAGGGTACCTGCATGAGGATAATA (SEQ ID NO: 36), respectively. Note that the 5'-upper primer 1 was designed so as to be in frame with GAL4DBD. PCR was carried out where (i) these oligonucleotides were used as primers and (ii) pGAL4-At2g36080 was used as a template, and a DNA fragment including the nucleotide sequence encoding the region 1-169 of the amino acid sequence encoded by At2g36080 gene was isolated. This DNA fragment was incorporated into 35S-GAL4DBD plasmid which had already been digested with restriction enzyme SmaI. Thereafter, the nucleotide sequence of the insert was determined. As a result, the insert was confirmed to consist of a sequence encoding a region including the region 1-169 of the already-reported amino acid sequence encoded by At2g36080 gene.

Note that the PCR was carried out under the same conditions as in (1-2-1).

(1-2-3) Construction of Effector Plasmid pGAL4-De 178 to 192 Including Nucleotide Sequence of At2g36080 Gene from which Region Encoding Amino Acids 178-192 is Deleted Oligonucleotides were synthesized so as to include sequences corresponding to (i) a 5'-upper primer 1 of At2g36080 gene: gATGTCAATAAACCAATACTCAAGC-GATTT (SEQ ID NO: 34), and (ii) a lower primer 3 of At2g36080 gene (that binds to the region 511-531 in the nucleotide sequence of At2g36080 gene): AGATCTA-GATCTTTGGCTCTCCACCGCTTG (SEQ ID NO: 37), respectively. Note that the 5'-upper primer 1 was designed so as to be in frame with GAL4DBD, and the lower primer 3 contained a BglII restriction site. PCR was carried out where (i) these oligonucleotides were used as primers and (ii) pGAL4-At2g36080 was used as a template, and a DNA fragment including the region 1-178 of the amino acid sequence encoded by At2g36080 gene was isolated. This DNA fragment was incorporated into 35S-GAL4DBD plasmid which had already been digested with restriction enzyme SmaI. Thereafter, the nucleotide sequence of the insert was determined. As a result, the insert was confirmed to consist of a sequence encoding a region including the region 1-178 of the already-reported amino acid sequence encoded by At2g36080 gene. Thus, pGAL4-1-178 plasmid was obtained.

Oligonucleotides were synthesized so as to include sequences corresponding to (i) an upper primer 2 (that binds to the region 577-598 in the nucleotide sequence of At2g36080 gene): agatctagatctCAGCTAGATTCG-GACTGGTC (SEQ ID NO: 38), and (ii) a 3'-lower primer 1 (that binds to the region 710-735 in the nucleotide sequence of At2g36080 gene): gtcgacgtcgacTTAGCTCGTCCGGT-TCATATCTCCT (SEQ ID NO: 35), respectively. Note that the upper primer 2 contained a BglII restriction site, and the 3'-lower primer 1 contained a SalI restriction site. PCR was carried out where (i) these oligonucleotides were used as primers and (ii) pGAL4-At2g36080 was used as a template, and a DNA fragment including the region 193-244 of the amino acid sequence encoded by At2g36080 gene was isolated. This DNA fragment was digested with restriction enzymes BglII and SalI, and a DNA fragment of interest was isolated therefrom through agarose gel electrophoresis. Then, this DNA fragment was incorporated into pGAL4-1-178 plasmid which had already been digested with restriction enzymes BglII and SalI. Thereafter, the nucleotide sequence of the insert was determined. As a result, the insert was confirmed to consist of a sequence encoding a protein including the already-reported amino acid sequence encoded by At2g36080 gene from which the region 178-192 was deleted.

Note that the PCR was carried out under the same conditions as in (1-2-1).

(1-2-4) Construction of Effector Plasmid pGAL4-178/192 Including Nucleotide Sequence Encoding Region 178-192 of Amino Acid Sequence Encoded by At2g36080

Oligonucleotides were synthesized so as to include sequences corresponding to (i) a partial sequence 1 of At2g36080 gene (SEQ ID NO: 39, corresponding to the region 532-576 in the nucleotide sequence of At2g36080 gene): aGGCAACTCGAAGACATTAAGACTGT-TCGGAGTGAACATGGAGT GCTAA, and (ii) a partial sequence 2 (SEQ ID NO: 40, corresponding to the sequence complementary to the region 532-576 in the nucleotide sequence of At2g36080 gene): TTAGCACTCCATGT-TCACTCCGAACAGTCTTAATGTCTTCGAGTT GCCT, respectively. Note that the partial sequence 1 was designed so as to be in frame with GAL4DBD, and the partial sequence 2 was a complementary sequence of the partial sequence 1. These oligonucleotides were mixed together. The resulting mixture was heated at 90° C. for two minutes, and was then heated at 60° C. for an hour. Thereafter, the mixture was left to stand at room temperature (25° C.) for two hours for annealing, so that a double-stranded DNA fragment was obtained. This DNA fragment was incorporated into 35S-GAL4DBD plasmid which had already been digested with restriction enzyme SmaI. Thereafter, the nucleotide sequence of the insert was determined. As a result, the insert was confirmed to consist of a sequence encoding a region including the region 178-192 of the already-reported amino acid sequence encoded by At2g36080 gene.

(1-3) Construction of Reporter Gene (A of FIG. 1)

(1-3-1) Construction of p35S-GAL4-LUC Reporter Gene (A of FIG. 1)

Plasmid pUC18 was digested with restriction enzymes EcoRI and SstI. Separately, plasmid pBI221 (available from Clontech) was digested with restriction enzymes EcoRI and SstI, and a 270-bp DNA fragment including a nopaline synthase terminator (Nos-ter) region was isolated through agarose gel electrophoresis. The resulting fragment was inserted into the EcoRI-SstI site of plasmid pUC18 that had already been digested with restriction enzymes EcoRI and SstI. Subsequently, complementary strands, DNA1: AGCTTA-GATCTGCAAGACCCTTCCTCTATATAAG-GAAGTTCATTT CATTTGGAGAGGACACGCTG (SEQ ID NO: 41) and DNA2: GATCCAGCGTGTCCTCTC-CAAATGAAATGAACTTCCTTATATAG AGGAAGGGTCTTGCAGATCTA (SEQ ID NO: 42), each including the TATA box of the cauliflower mosaic virus 35S promoter, were synthesized.

The DNAs thus synthesized were heated at 90° C. for two minutes, and were then heated at 60° C. for an hour. Thereafter, the DNAs were left to stand at room temperature (25° C.) for two hours for annealing, so as to prepare double-stranded DNA. Plasmid pUC18 including Nos-ter was digested with restriction enzymes HindIII and BamHI. The synthesized double-stranded DNA was inserted into the HindIII-BamHI site of pUC18. Thus, a plasmid including the TATA-box and Nos-ter was constructed.

The plasmid thus constructed was digested with restriction enzyme SstI, and was then blunt-ended with T4 DNA polymerase.

Plasmid vector PGV-CS2 (available from Toyo Ink Mfg. Co., Ltd.) having the firefly luciferase gene (LUC) was digested with restriction enzymes XbaI and NcoI, and was then blunt-ended with T4 DNA polymerase. Thereafter, a 1.65 kb-DNA fragment including the luciferase gene was isolated and purified through agarose gel electrophoresis. This DNA fragment was inserted into the above plasmid including the TATA box and the Nos terminator. Thus, reporter gene pTATA-LUC was constructed.

Plasmid pG5CAT (available from Clontech) having five repeats of the DNA binding sequence of the yeast GAL4 protein was digested with restriction enzymes SmaI and XbaI, and was then blunt-ended with T4 DNA polymerase. Thereafter, a DNA fragment including five repeats of the DNA binding sequence of the GAL4 protein was purified through agarose gel electrophoresis. TATA-LUC vector was digested with restriction enzyme BglII, and was then blunt-ended with T4 DNA polymerase. Into this site, the blunt-ended DNA fragment including five repeats of the DNA binding sequence of the GAL4 protein was inserted. Then, among the resulting plasmids, the one in which the DNA binding sequence of the GAL4 protein was in the forward direction was selected. Thus, reporter gene pGAL4-LUC was constructed.

Further, PCR was carried out by using (i) plasmid pBI1221 as a template and (ii) a 5'-upper primer (CGC-CAGGGTTTTCCCAGTCACGAC (SEQ ID NO: 43)) and a 3'-lower primer (AAGGGTAAGCTTAAGGATAGTGG-GATTGTGCGTCATC (SEQ ID NO: 44)), and a DNA fragment including the region from −800 to −46 of the CaMV 35S promoter was obtained. The DNA fragment thus obtained was digested with restriction enzyme HindIII, and a 760-bp DNA fragment including the region from −800 to −46 of the CaMV 35S promoter was isolated through agarose gel electrophoresis. This HindIII fragment was inserted into reporter gene pGAL4-LUC which had already been digested with restriction enzyme HindIII. Then, one in which CaMV 35S promoter DNA was in the forward direction was selected. Thus, p35S-GAL4-LUC reporter gene was constructed (see A of FIG. 1).

(1-4) Construction of Reference Gene

Cassette vector pRL-null (available from Promega) having *Renilla* luciferase gene was cleaved with restriction enzymes NheI and XbaI, and was then blunt-ended with T4 DNA polymerase. Thereafter, a 948-bp DNA fragment including *Renilla* luciferase gene was purified through agarose gel electrophoresis. This DNA fragment was inserted into pBI221 vector at a region from which GUS gene had been removed, which pBI221 vector was used to construct the effector plasmids. Then, among the resulting plasmids, the one in which *Renilla* luciferase gene was in the forward direction was selected (construction of pPTRL).

(1-5) Method for Assaying Activity of Reporter Gene

The reporter gene and each of the effector plasmids were introduced into *Arabidopsis thaliana* by the particle gun method. Then, effects of the effector plasmid were analyzed by assaying activity of the reporter gene.

(1-6) Introduction of Gene by Particle Gun

Gold grains (510 mg, 1 mm in diameter; available from Bio-Rad) were coated with (i) 1.6 mg of p35S-GAL4-LUC reporter gene prepared as above, (ii) 1.2 mg of DNA of one of effector plasmids pGAL4DB-RD prepared as above, and (iii) 0.4 mg of the reference gene plasmid. *Arabidopsis thaliana* leaves (seven leaves) of 21 day-old were laid out on a water-moistened filter paper in a 9-cm petri dish, and DNA was introduced thereto with use of the PDS-1000/He device for particle bombardment (available from Bio-Rad). The leaves were left to stand at 22° C. for six hours in bright light. After that, activity of the reporter gene was assayed.

(1-7) Assay of Luciferase Activity

The *Arabidopsis thaliana* leaves which had been left to stand for six hours were ground in liquid nitrogen, and were then suspended in 200 μl of the Passive Lysis Buffer from the Dual-Luciferase (Registered Trademark) Reporter Assay System (available from Promega). The resultant was centrifuged to obtain the supernatant. This cell extract (20 μl) was mixed with 100 μl of the assay buffer attached to the Dual-Luciferase (Registered Trademark) Reporter Assay System (available from Promega), and luciferase activity of the cell extract was assayed with use of a luminometer (TD 20/20; available from Turner Design). Specifically, in accordance with the instructions of the assay kit, activities of the respective firefly luciferase and *Renilla* luciferase were assayed by measuring luminescence over 10 seconds in the integral mode. An activity value indicating the activity of the reference gene was divided by an activity value indicating the activity of the reporter gene, and a relative luciferase activity thus found, which is a relative value, was determined as a measured value. In this experiment, each type of the effector plasmids was subjected to a transient assay three times, so that an average value and a standard deviation were found. Effects of the effector plasmids were analyzed as follows: A relative activity value of p35S-GAL4-LUC reporter gene obtained in a case where PUC18 was introduced as an effector was defined as "1". Then, effects of each of the effector plasmids (constructed by fusing GAL4DBD to various DNA fragments) were evaluated based on variations in an activity value of the reporter gene, which variations were observed when the effector plasmid and the reporter gene were concurrently introduced into cells. Namely, if the activity value of the reporter gene decreases in response to introduction of p35S-GAL4-LUC reporter gene and the effector plasmid including DNA encoding one of the peptide sequences, such decrease indicates that the peptide has the effect of repressing the activity of the reporter gene (repressor function). In the below-described "Identification of Repressor Domain", the activity of the reporter gene was assayed. If a relative activity value of p35S-GAL4-LUC reporter gene was 1 or smaller, the effector plasmid was determined to have the repressor function.

(1-8) Identification of Repressor Domain

A of FIG. 1 shows the structure of the reporter gene and the structures of the respective effector plasmids. B of FIG. 1 shows the results of the assay of the activity of the reporter gene.

As shown in B of FIG. 1, (i) the effector plasmid including the full length of At2g36080 and (ii) the effector plasmid including the nucleotide sequence encoding the region 178-192 of the amino acid sequence encoded by At2g36080 gene decreased the activity of the reporter gene by 75% to 90% or more, in comparison with the case where PUC18 was introduced as an effector (control). This demonstrates that these peptides have transcriptional repression activity. On the other hand, (i) the peptide consisting of the region 1-169 of the amino acid sequence encoded by AT2G36080 and (ii) the effector plasmid including the nucleotide sequence of At2g36080 gene from which the region encoding the amino acids 178-192 was deleted did not decrease the activity of the reporter gene. This indicates that the region of At2g36080 gene which region included the nucleotide sequence encoding the region 178-192 in the amino acid sequence encoded by At2g36080 gene and was bound to the GAL4 DNA-binding domain served as a repressor for repressing transcription.

Example 2

Identification of Peptide Serving as Repression Domain (2-1) Construction of Effector Plasmid pGAL4-183/192 Including Nucleotide Sequence Encoding Region 183-192 of Amino Acid Sequence Encoded by At2g36080

Oligonucleotides were synthesized so as to include sequences corresponding to (i) a partial sequence 3 of At2g36080 gene (SEQ ID NO: 45, corresponding to the region 547-576 in the nucleotide sequence of At2g36080 gene): TTAAGACTGTTCGGAGTGAACATGTAA, and (ii) a partial sequence 4 (SEQ ID NO: 46, corresponding to the sequence complementary to the region 547-576 in the nucleotide sequence of At2g36080 gene): TTACATGTTCACTC-CGAACAGTCTTAA, respectively. Note that the partial sequence 3 was designed so as to be in frame with GAL4DBD, and the partial sequence 4 was a complementary sequence of the partial sequence 3. These oligonucleotides were mixed together. The resulting mixture was heated at 90° C. for two minutes, and was then heated at 60° C. for an hour. Thereafter, the mixture was left to stand at room temperature (25° C.) for two hours for annealing, so that a double-stranded DNA fragment was obtained. This DNA fragment was incorporated into 35S-GAL4DBD plasmid which had already been digested with restriction enzyme SmaI. Thereafter, the nucleotide sequence of the insert was determined. As a result, the insert was confirmed to consist of a sequence encoding a region including the region 178-192 of the already-reported amino acid sequence encoded by At2g36080 gene.

(2-2) Introduction of Gene and Assay of Luciferase Activity

In the same manner as in (1-3-1) of Example 1, p35S-GAL4-LUC reporter gene was constructed. Further, according to the method described in (1-4) of Example 1, a reference gene (pPTRL) was constructed.

In the same manner as in the method for assaying activity of the reporter gene described in (1-5) of Example 1, the reporter gene and each of the effector plasmids were introduced into Arabidopsis thaliana by the particle gun method in the same manner as in (1-6) of Example 1. Then, effects of each of the effector plasmids were analyzed by assaying activity of the reporter gene.

Luciferase activity of the cell extract of the Arabidopsis thaliana leaves which had been left to stand for six hours was assayed in the same manner as that in the assay of the luciferase activity described in (1-7) of Example 1. Then, a relative luciferase activity thereof was found as a measured value. In this experiment, each type of the effector plasmids was subjected to a transient assay three times, so that an average value and a standard deviation were found. Effects of the effector plasmids were analyzed as follows: A relative activity value of p35S-GAL4-LUC reporter gene obtained in a case where PUC18 was introduced as an effector was defined as "1". Then, effects of each of the effector plasmids (constructed by fusing GAL4DBD to various DNA fragments) were evaluated based on variations in an activity value of the reporter gene, which variations were observed when the effector plasmid and the reporter gene were concurrently introduced into cells. Namely, if the activity value of the reporter gene decreases in response to introduction of p35S-GAL4-LUC reporter gene and effector plasmid pGAL4DB-RD including DNA encoding one of the peptide sequences, such decrease indicates that the peptide has the effect of repressing the activity of the reporter gene (repressor function). In the below-described "Identification of Repressor Domain", the activity of the reporter gene was assayed. If the relative activity value of p35S-GAL4-LUC reporter gene was 1 or smaller, the effector plasmid was determined to have the repressor function.

(2-3) Identification of Repressor Domain

C of FIG. 1 shows the structure of the reporter gene and the structures of the respective effector plasmids. D of FIG. 1 shows the results of the assay of the activity of the reporter gene.

As shown in D of FIG. 1, (i) the effector plasmid including the region 178-192 of the amino acid sequence encoded by At2g36080 gene and (ii) the effector plasmid including the region 183-192 of the amino acid sequence encoded by At2g36080 gene decreased the activity of the reporter gene by 87% to 97% or more, in comparison with a case where PUC18 was introduced as an effector (control). This demonstrates that these peptides have transcriptional repression activity.

This indicates that the At2g36080 gene fragment (183-190 aa.) bound to the GAL4 DNA-binding domain served as a repressor for repressing transcription.

Example 3

Transcriptional Repression by Effector Plasmid Including Gene Including Nucleotide Sequence Encoding Amino Acid Sequence R/KLFGV (SEQ ID NO. 77)

(3-1) Construction of Effector Plasmids
(3-1-1) Construction of Effector Plasmid pGAL4-At3g11580 Including Entire Protein-Coding Region of At3g11580 Gene Oligonucleotides were synthesized so as to include sequences corresponding to the sequences on the respective 5'- and the 3'-ends of the protein-coding region of At3g11580 gene of Arabidopsis thaliana, whose nucleotide sequence has already been reported. One of the oligonucleotides included a sequence corresponding to a 5'-upper primer of At3g11580 gene (SEQ ID NO: 47, corresponding to the region 1-29 in the nucleotide sequence of At3g11580 gene): gATGTCAGT- CAACCATTACCACAACACTCT. Note that the 5'-upper primer was designed so as to be in frame with GAL4DBD. The other of the oligonucleotides included a sequence corresponding to a 3'-lower primer (SEQ ID NO: 48, corresponding to the region 782-804 in the nucleotide sequence of At3g11580 gene): GTCGACGTCGACtcaACCTCGTC-CATCTCCTACCTG. Note that the 3'-lower primer contained a SalI restriction site. PCR was carried out where (i) these oligonucleotides were used as primers and (ii) cDNA derived from the seedling of *Arabidopsis thaliana* was used as a template, and a DNA fragment including the protein-coding region of At3g11580 gene was isolated. This DNA fragment was digested with restriction enzyme SalI, and a DNA fragment of interest was isolated therefrom through agarose gel electrophoresis. Then, the DNA fragment thus isolated was incorporated into 35S-GAL4DBD plasmid which had already been digested with restriction enzymes SmaI and SalI. Thereafter, the nucleotide sequence of the insert was determined. As a result, the insert was confirmed to be the already-reported protein-coding region of At3g11580 gene. Note that the PCR was carried out under the following conditions: 30 cycles each consisting of denaturation at 94° C. for one minute; annealing at 50° C. for one minute; and elongation at 72° C. for three minutes.

(3-1-2) Construction of Effector Plasmid pGAL4-At2g46870 Including Entire Protein-Coding Region of At2g46870 Gene Oligonucleotides were synthesized so as to include sequences corresponding to the sequences on the respective 5'- and the 3'-ends of the protein-coding region of At2g46870 gene of *Arabidopsis thaliana*, whose nucleotide sequence has already been reported. One of the oligonucleotides included a sequence corresponding to a 5'-upper primer of At2g46870 gene (SEQ ID NO: 49, corresponding to the region 1-29 in the nucleotide sequence of At2g46870 gene): gATGATGACA-GATTTATCTCTCACGAGAGA. Note that this 5'-upper primer was designed so as to be in frame with GAL4DBD. The other of the oligonucleotides included a sequence corresponding to a 3'-lower primer (SEQ ID NO: 50, corresponding to the region 910-933 in the nucleotide sequence of At2g46870 gene): TTATTGATCCAAATCAAAAGACAA. PCR was carried out where (i) these oligonucleotides were used as primers and (ii) cDNA derived from the pod of *Arabidopsis thaliana* was used as a template, and a DNA fragment including the protein-coding region of At2g46870 gene was isolated. The DNA fragment thus isolated was incorporated into 35S-GAL4DBD plasmid which had already been digested with restriction enzyme SmaI. Thereafter, the direction and the nucleotide sequence of the insert were determined. As a result, the insert was confirmed to be the already-reported protein-coding region of At2g46870 gene. Note that the PCR was carried out under the same conditions as in (3-1-1).

(3-1-3) Construction of Effector Plasmid pGAL4-At1g13260 Including Entire Protein-Coding Region of At1g13260 Gene Oligonucleotides were synthesized so as to include sequences corresponding to the sequences on the respective 5'- and the 3'-ends of the protein-coding region of At1g13260 gene of *Arabidopsis thaliana*, whose nucleotide sequence has already been reported. One of the oligonucleotides included a sequence corresponding to a 5'-upper primer of At1g13260 gene (SEQ ID NO: 51, corresponding to the region 1-22 in the nucleotide sequence of At1g13260 gene): GATGGAATC-GAGTAGCGTTGATG. Note that this 5'-upper primer was designed so as to be in frame with GAL4DBD. The other of the oligonucleotides included a sequence corresponding to a 3'-lower primer (SEQ ID NO: 52, corresponding to the region 1012-1035 in the nucleotide sequence of At1g13260 gene): TTACGAGGCGTGAAAGATGCGTTG. PCR was carried out where (i) these oligonucleotides were used as primers and (ii) cDNA derived from the seedling of *Arabidopsis thaliana* was used as a template, and a DNA fragment including the protein-coding region of At1g13260 gene was isolated. The DNA fragment thus isolated was incorporated into 35S-GAL4DBD plasmid which had already been digested with restriction enzyme SmaI. Thereafter, the direction and the nucleotide sequence of the insert were determined. As a result, the insert was confirmed to be the already-reported protein-coding region of At1g13260 gene. Note that the PCR was carried out under the same conditions as in (3-1-1).

(3-1-4) Construction of Effector Plasmid pGAL4-At1g68840 Including Entire Protein-Coding Region of At1g68840 Gene Oligonucleotides were synthesized so as to include sequences corresponding to the sequences on the respective 5'- and the 3'-ends of the protein-coding region of At1g68840 gene of *Arabidopsis thaliana*, whose nucleotide sequence has already been reported. One of the oligonucleotides included a sequence corresponding to a 5'-upper primer of At1g68840 gene (SEQ ID NO: 53, corresponding to the region 1-22 in the nucleotide sequence of At1g68840 gene): GATGGAT-TCTAGTTGCATAGACG. Note that this 5'-upper primer was designed so as to be in frame with GAL4DBD. The other of the oligonucleotides included a sequence corresponding to a 3'-lower primer (SEQ ID NO: 54, corresponding to the region 1035-1059 in the nucleotide sequence of At1g68840 gene): TTACAAAGCATTGATTATCGCCTGC. PCR was carried out where (i) these oligonucleotides were used as primers and (ii) cDNA derived from the seedling of *Arabidopsis thaliana* was used as a template, and a DNA fragment including the protein-coding region of At1g68840 gene was isolated. The DNA fragment thus isolated was incorporated into 35S-GAL4DBD plasmid which had already been digested with restriction enzyme SmaI. Thereafter, the direction and the nucleotide sequence of the insert were determined. As a result, the insert was confirmed to be the already-reported protein-coding region of At1g68840 gene. Note that the PCR was carried out under the same conditions as in (3-1-1).

(3-1-5) Construction of Effector Plasmid pGAL4-At4g36990 Including Entire Protein-Coding Region of At4g36990 Gene Oligonucleotides were synthesized so as to include sequences corresponding to the sequences on the respective 5'- and the 3'-ends of the protein-coding region of At4g36990 gene of *Arabidopsis thaliana*, whose nucleotide sequence has already been reported. One of the oligonucleotides included a sequence corresponding to a 5'-upper primer 1 of At4g36990 gene (SEQ ID NO: 55, corresponding to the region 1-29 in the nucleotide sequence of At4g36990 gene): gATGACGGCT-GTGACGGCGGCGCAAAGATC. Note that this 5'-upper primer 1 was designed so as to be in frame with GAL4DBD. The other of the oligonucleotides included a sequence corresponding to a 3'-lower primer 1 (SEQ ID NO: 56, corresponding to the region 823-855 in the nucleotide sequence of At4g36990 gene):

```
gtcgacgtcgacTTAGTTGCAGACTTTGCTGCTTTTCCACAACGG.
```

Note that this 3'-lower primer 1 contained a SalI restriction site. PCR was carried out where (i) these oligonucleotides were used as primers and (ii) cDNA derived from the root of *Arabidopsis thaliana* was used as a template, and a DNA fragment including the protein-coding region of At4g36990 gene was isolated. This DNA fragment was digested with restriction enzyme SalI, and a DNA fragment of interest was isolated therefrom through agarose gel electrophoresis. Then, the DNA fragment thus isolated was incorporated into 35S-GAL4DBD plasmid which had already been digested with restriction enzymes SmaI and SalI. Thereafter, the nucleotide sequence of the insert was determined. As a result, the insert was confirmed to be the already-reported protein-coding region of At4g36990 gene. Note that the PCR was carried out under the same conditions as in (3-1-1).

(3-1-6) Construction of Effector Plasmid pGAL4-At4g11660 Including Entire Protein-Coding Region of At4g11660 Gene Oligonucleotides were synthesized so as to include sequences corresponding to the sequences on the respective 5'- and the 3'-ends of the protein-coding region of At4g11660 gene of *Arabidopsis thaliana*, whose nucleotide sequence has already been reported. One of the oligonucleotides included a sequence corresponding to a 5'-upper primer of At4g11660 gene (SEQ ID NO: 57, corresponding to the region 1-29 in the nucleotide sequence of At4g11660 gene): gATGCCGGGG-GAACAAACCGGAGAAACTCC. Note that this 5'-upper primer was designed so as to be in frame with GAL4DBD. The other of the oligonucleotides included a sequence corresponding to a 3'-lower primer (SEQ ID NO: 58, corresponding to the region 1108-1134 in the nucleotide sequence of At4g11660 gene): gtcgacgtcgacTCATTTTCCGAGT-TCAAGCCACGACCC. Note that this 3'-lower primer contained a SalI restriction site. PCR was carried out where (i) these oligonucleotides were used as primers and (ii) cDNA derived from the root of *Arabidopsis thaliana* was used as a template, and a DNA fragment including the protein-coding region of At4g11660 gene was isolated. This DNA fragment was digested with restriction enzyme SalI, and a DNA fragment of interest was isolated therefrom through agarose gel electrophoresis. The DNA fragment thus isolated was incorporated into 35S-GAL4DBD plasmid which had already been digested with restriction enzymes SmaI and SalI. Thereafter, the nucleotide sequence of the insert was determined. As a result, the insert was confirmed to be the already-reported protein-coding region of At4g11660 gene. Note that the PCR was carried out under the same conditions as in (3-1-1).

(3-2) Introduction of Gene and Assay of Luciferase Activity

In the same manner as in (1-3-1) of Example 1, p35S-GAL4-LUC reporter gene was constructed. Further, according to the method described in (1-4) of Example 1, a reference gene (pPTRL) was constructed.

In the same manner as in the method for assaying activity of the reporter gene described in (1-5) of Example 1, the reporter gene and each of the effector plasmids were introduced into *Arabidopsis thaliana* by the particle gun method in the same manner as in (1-6) of Example 1. Then, effects of each of the effector plasmids were analyzed by assaying activity of the reporter gene.

Luciferase activity of the cell extract of the *Arabidopsis thaliana* leaves which had been left to stand for six hours was assayed in the same manner as that in the assay of luciferase activity described in (1-7) of Example 1. Then, a relative luciferase activity thereof was found as a measured value. In this experiment, each type of the effector plasmids was subjected to a transient assay three times, so that an average value and a standard deviation were found. Effects of the effector plasmids were analyzed as follows: A relative activity value of p35S-GAL4-LUC reporter gene obtained in a case where p35S-GAL4DBD was introduced as an effector was defined as "1". Then, effects of each of the effector plasmids (constructed by fusing GAL4DBD to various DNA fragments) were evaluated based on variations in an activity value of the reporter gene, which variations were observed when the effector plasmid and the reporter gene were concurrently introduced into cells. Namely, if the activity value of the reporter gene decreases in response to introduction of p35S-GAL4-LUC reporter gene and effector plasmid pGAL4DB-RD including DNA encoding one of the peptide sequences, such decrease indicates that the peptide has the effect of repressing the activity of the reporter gene (repressor function). In the below-described "Identification of Repressor", the activity of the reporter gene was assayed. If the relative activity value of p35S-GAL4-LUC reporter gene was 1 or smaller, the effector plasmid was determined to have the repressor function.

(3-3) Identification of Repressor

A through G of FIG. 2 show the results of the assay of the activity of the reporter gene.

As shown in A through G of FIG. 2, the effector plasmids including respective peptides obtained by fusing, with GAL4DBD, the gene regions of respective At3g11580 gene, At2g46870 gene, At1g13260 gene, At1g68840 gene, At4g36990 gene, and At4g11660 gene, which gene regions encoded their respective proteins each including the amino acid sequence "R/KLFGV" (SEQ ID NO. 77), decreased the activity of the reporter gene by 82% to 96%, in comparison with a case where p35S-GAL4DBD was introduced as an effector (control). This demonstrates that these peptides have transcriptional repression activity. This indicates that At3g11580 gene, At2g46870 gene, At1g13260 gene, At1g68840 gene, At4g36990 gene, and At4g11660 gene each of which was bound to the GAL4 DNA-binding domain served as a repressor for repressing transcription.

Example 4

Identification of Repression Domain of At4g36990

(4-1) Constructions of Effector Plasmids
(4-1-1) Construction of Effector Plasmid pGAL4-At4g36990-233/243 Including Nucleotide Sequence Encoding Region 233-243 of Amino Acid Sequence Encoded by At4g36990

Oligonucleotides were synthesized so as to include sequences corresponding to (i) a partial sequence 1 of At4g36990 gene (SEQ ID NO: 59, corresponding to the region 697-729 in the nucleotide sequence of At4g36990 gene, and having a SalI restriction site on its 3'-end): gGGT-GAAGGATTGAAATTGTTTGGGGTGTGGT-TGgtcgacgtcgac, and (ii) a partial sequence 2 (SEQ ID NO: 60, corresponding to the sequence complementary to the region 697-729 in the nucleotide sequence of At4g36990 gene, and having a SalI restriction site on its 5'-end): GTC-GACGTCGACCAACCACACCCCAAA-CAATTTCAATCCTTCAC CC, respectively. Note that the partial sequence 1 was designed so as to be in frame with GAL4DBD, and the partial sequence 2 was a complementary sequence of the partial sequence 1. These oligonucleotides were mixed together. The resulting mixture was heated at 90° C. for two minutes, and was then heated at 60° C. for an hour. Thereafter, the mixture was left to stand at room temperature (25° C.) for two hours for annealing, so that a double-stranded DNA fragment was obtained. This DNA fragment was incorporated into 35S-GAL4DBD plasmid which had already been digested with restriction enzyme SmaI. Thereafter, the direction and the nucleotide sequence of the insert were determined. As a result, the insert was confirmed to consist of a sequence encoding a region including the region 233-243 of the already-reported amino acid sequence encoded by At4g36990 gene.

(4-1-2) Construction of Effector Plasmid pGAL4-mut236-243 Including Nucleotide Sequence Encoding Amino Acid Sequence Encoded by At4g36990 Gene with Mutation in Amino Acids 236-243

Oligonucleotides were synthesized so as to include sequences corresponding (i) a 5'-upper primer 1 of At4g36990 gene (SEQ ID NO: 55, corresponding to the region 1-29 in the nucleotide sequence of At4g36990 gene: gATGACGGCTGTGACGGCGGCGCAAAGATC, and (ii) a lower primer 2 (SEQ ID NO: 61, corresponding to the region 680-705 in the nucleotide sequence of At4g36990 gene): CCCCCCGCGGCTCCAGCTCCTTCACCTACCCCCTCCTCTGC, respectively. Note that the 5'-upper primer 1 was designed so as to be in frame with GAL4DBD. PCR was carried out where (i) these oligonucleotides were used as primers and (ii) pGAL4-At4g36990 was used as a template, and a DNA fragment including the nucleotide sequence encoding the region 1-236 of the amino acid sequence encoded by At4g36990 gene was isolated. This DNA fragment was incorporated into 35S-GAL4DBD plasmid which had already been digested with restriction enzyme SmaI. Thereafter, the nucleotide sequence of the insert was determined. As a result, the insert was confirmed to consist of a sequence encoding a region including the region 1-236 of the already-reported amino acid sequence encoded by At4g36990 gene. Thus, plasmid pGAL4-1-236 was obtained. Next, oligonucleotides were synthesized as to include sequences corresponding to (i) an upper primer 2 (SEQ ID NO: 62, binding to the region 732-752 in the nucleotide sequence of At4g36990 gene): gggccgcggggggct-tgggctAAAGGAGAGAGAAAAAAGAGGG, and (ii) a 3'-lower primer 1 (SEQ ID NO: 56, binding to the region 823-855 in the nucleotide sequence of At4g36990 gene): gtcgacgtcgacTTAGTTGCA-GACTTTGCTGCTTTTCCACAACGG, respectively. Note that the 3'-lower primer 1 contained a SalI restriction site. PCR was carried out where (i) these oligonucleotides were used as primers and (ii) pGAL4-At4g36990 was used as a template, and a DNA fragment including the nucleotide sequence encoding the region 244-283 of the amino acid sequence encoded by At4g36990 gene was isolated. This DNA fragment was digested with restriction enzyme SalI, and a DNA fragment of interest was isolated therefrom through agarose gel electrophoresis. The DNA fragment thus isolated was incorporated into pGAL4-1-236 plasmid which had already been digested with restriction enzymes SmaI and SalI. Thereafter, the nucleotide sequence of the insert was determined. As a result, the insert was confirmed to consist of a sequence encoding the already-reported amino acid sequence encoded by At4g36990 gene with mutation in the amino acids 236-243.

Note that the PCR was carried out under the following conditions: 30 cycles each consisting of denaturation at 94° C. for one minute; annealing at 50° C. for one minute; and elongation at 72° C. for three minutes.

(4-2) Introduction of Gene and Assay of Luciferase Activity

In the same manner as in (1-3-1) of Example 1, p35S-GAL4-LUC reporter gene was constructed. Further, according to the method described in (1-4) of Example 1, a reference gene (pPTRL) was constructed.

In the same manner as in the method for assaying activity of the reporter gene described in (1-5) of Example 1, the reporter gene and each of the effector plasmids were introduced into *Arabidopsis thaliana* by the particle gun method in the same manner as in (1-6) of Example 1. Then, effects of each of the effector plasmids were analyzed by assaying activity of the reporter gene.

Luciferase activity of the cell extract of the *Arabidopsis thaliana* leaves which had been left to stand for six hours was assayed in the same manner as that in the assay of luciferase activity described in (1-7) of Example 1. Then, a relative luciferase activity thereof was found as a measured value. In this experiment, each type of the effector plasmids was subjected to a transient assay three times, so that an average value and a standard deviation were found. Effects of the effector plasmids were analyzed as follows: A relative activity value of p35S-GAL4-LUC reporter gene obtained in a case where PUC18 was introduced as an effector was defined as "1". Then, effects of each of the effector plasmids (constructed by fusing GAL4DBD to various DNA fragments) were evaluated based on variations in an activity value of the reporter gene, which variations were observed when the effector plasmid and the reporter gene were concurrently introduced into cells. Namely, if the activity value of the reporter gene decreases in response to introduction of p35S-GAL4-LUC reporter gene and effector plasmid pGAL4DB-RD including DNA encoding one of the peptide sequences, such decrease indicates that the peptide has the effect of repressing the activity of the reporter gene (repressor function). In the below-described "Identification of Repressor", the activity of the reporter gene was assayed. If the relative activity value of p35S-GAL4-LUC reporter gene was 1 or smaller, the effector plasmid was determined to have the repressor function.

(4-3) Identification of Repressor

B of FIG. 3 shows the results of the assay of the activity of the reporter gene.

As shown in B of FIG. 3, (i) the effector plasmid including the full length of AT4g36990 gene and (ii) the effector plasmid including the nucleotide sequence encoding the region 233-243 of the amino acid sequence encoded by AT4g36990 gene decreased the activity of the reporter gene by 60% to 80%, in comparison with a case where PUC18 was introduced as an effector (control). This demonstrates that these peptides have transcriptional repression activity. On the other hand, the effector plasmid including the nucleotide sequence encoding the amino acid sequence encoded by AT4g36990 gene with mutation in the amino acids 236-243 did not decrease the activity of the reporter gene. This indicates that the amino acids 233-243 in the amino acid sequence encoded by AT4g36990 gene served as a repressor domain for transcriptional repression.

Example 5

Effects of Gene Fragment Encoding At2g36080 Repression Domain 178-192 in Repressing Transcription Activation of AG in Plants (5-1) Construction of Vector pBIG2 for Transformation Plasmid p35S-GFP (available from Clontech, the U.S.A.) was cleaved with restriction enzymes HindIII and BamHI. Then, a DNA fragment including the cauliflower mosaic virus 35S promoter (CaMV 35S) was separated and obtained therefrom through agarose gel electrophoresis. Next, vector pBIG-HYG for plant transformation which was provided by Michigan State University, the U.S.A. (Becker, D. 1990 Nucleic Acid Research, 18:203) was cleaved with restriction enzymes HindIII and SstI. Then, a DNA fragment from which GUS gene was removed through agarose gel electrophoresis was obtained.

DNAs were synthesized so that they included the following sequences, respectively: 5'-GATCCACAATTACCAACAA-CAACAAACAACAAACAACATTACA ATTACAGATC-CCGGGGGTACCGTCGACGAGCTC-3' (SEQ ID NO: 63); and 5'-CGTCGACGGTACCCCCGGGATCTGTAAT-TGTAATGTTGTTTG TTGTTTGTTGTTGTTGGTAAT-TGT-3' (SEQ ID NO: 64). These DNAs were heated at 70° C. for 10 minutes, and were annealed by natural cooling, so that double-stranded DNA was obtained. This DNA fragment included (i) a BamHI restriction site on its 5'-end, (ii) an omega sequence derived from the tobacco mosaic virus for improving translation efficiency, and (iii) a SmaI restriction site and a SalI restriction site.

The double-stranded DNA thus synthesized and the DNA fragment including the CaMV 35S promoter region were inserted into the HindIII-SstI site of pBIG-HYG from which GUS gene had been removed. Thus, vector pBIG2 for plant transformation was obtained.

(5-2) Construction of Vector pAG36RD for Transformation

The following two DNA sequences, complementary to each other, were annealed: 5'-GGGAGGCAACTCGAAGA-CATTAAGACTGTTCGGAGTGAACA TGGAGTGCTAA-3' (SEQ ID NO: 65, corresponding to a partial nucleotide sequence (the region 532-576) of At2g36080 to which "GGG" was added at its 5'-end and a stop codon was added at its 3'-end); and 5'-TTAGCACTCCATGTTCACTCCGAA-CAGTCTTAATGTCTTCGA GTTGCCTCCC-3' (SEQ ID NO: 66). The resulting double-stranded DNA was inserted into pBIG2 vector that had been cleaved with SmaI. Then, the sequence thereof was confirmed, and the one into which the double-stranded DNA had been inserted in a forward direction was selected. Thus, p36RD was obtained.

RNA was extracted from the bud of *Arabidopsis thaliana*, and was then reverse-transcribed to prepare cDNA. The cDNA thus prepared was used as a template to carry out PCR, in which a 5'-upper primer gATGACCGCGTACCAATCG-GAGCTAGGAGG (SEQ ID NO: 67) and a 3'-lower primer CACTAACTGGAGAGCGGTTTGGTCTTGGCG (SEQ ID NO: 68) were used. Note that the PCR was carried out under the same conditions as in above-described examples. Consequently, a full sequence of AGAMOUS (the nucleotide sequence 1-759, the amino acids 1-252) was amplified, which was then inserted into p36RD obtained by cleavage with SmaI and agarose gel electrophoresis. Then, the sequence thereof was confirmed. Among the resultants into which AG gene was introduced in a forward direction, the one in which AG gene was in frame with 36RD was selected. Thus, pAG36RD was obtained.

(5-3) Transformation of Plant with pAG36RD

*Arabidopsis thaliana* was transformed with pAG36RD in accordance with "Transformation of *Arabidopsis thaliana* by vacuum infiltration, except that infiltration was carried out merely by immersion, not under vacuum. Plasmid pAG36RD was introduced into soil bacteria (*Agrobacterium tumefaciens* strain GV3101 (C58C1Rifr) pMP90 (Gmr) (koncz and Schell 1986)) by electroporation. The bacteria into which plasmid pAG36RD was introduced were cultured in a 250-ml LB medium for two days.

Subsequently, the bacteria were collected from the culture solution, and were suspended in 500-ml infiltration medium. In this solution, *Arabidopsis thaliana* that had been grown for 14 days was immersed for one minute for infiltration, and the infiltrated *Arabidopsis thaliana* was then allowed to grow until fruition. Seeds were collected therefrom, and were sterilized with a 50% bleach/0.02% Triton X-100 solution for seven minutes. Then, the seeds were rinsed three times with sterilized water, and the seeds thus sterilized were sowed on a ½ MS selection medium containing 30 mg/l hygromycin.

On the hygromycin plate, transformed plants to be grown were selected. Then, the transformed plants thus selected were planted in soil and grown.

(5-4) Traits of Plants Transformed with pAG36RD

C of FIG. 4 shows the trait of the plant transformed with pAG36RD. The flower of the plant transformed with pAG36RD was confirmed to exhibit the morphology of an increased number of petals (so-called "double flower"). This morphology is similar to those of (i) the flower of the plant transformed with pAGSRDX (shown in B of FIG. 4) and (ii) the flower of the ag mutant. This demonstrates that a 36RD (GNSKTLRLFGVNMEC, SEQ ID NO: 3) peptide fragment imparts transcriptional repression activity to a transcriptional activator by fusing thereto.

Example 6

Effects of Gene Fragment Encoding At2g36080 Repression Domain 178-192 in Repressing Transcription Activation of CUC2 and CUC1 (Redundant with CUC2) in Plants (6-1) Construction of Vector pCUC2-36RD for Transformation In the same manner as in (5-1) and (5-2) of Example 5, a partial nucleotide sequence of AT2G36080 (corresponding to the region 532-576) was inserted into vector pBIG2 for transformation so that the partial nucleotide sequence was in a forward direction. Thus, p36RD was obtained.

RNA was extracted from the cane top of *Arabidopsis thaliana*, and was then reverse-transcribed to prepare cDNA. The cDNA thus prepared was used as a template to carry out PCR, with use of a 5'-upper primer GGGATGGACATTCCG-TATTACCACTAC (SEQ ID NO: 69) and a 3'-lower primer GTAGTTCCAAATACAGTCAAGTC (SEQ ID NO: 70), which was prepared by removing the stop codon from the 3'-end of CUC2 gene. Note that the PCR was carried out under the same conditions as in above-described examples. Consequently, a full sequence of CUC2 (the nucleotide sequence 1-1128, the amino acids 1-375) was amplified, which was then inserted into p36RD obtained by cleavage with SmaI and agarose gel electrophoresis. Then, the sequence thereof was confirmed. Among the resultants into which CUC2 gene was introduced in a forward direction, the one in which CUC2 gene was in frame with 36RD was selected. Thus, pCUC2-36RD was obtained.

(6-2) Transformation of Plant with pCUC2-36RD

In the same manner as in (5-3) of Example 5, *Arabidopsis thaliana* was transformed with pCUC2-36RD. Among the resulting transformed plants, transformed plants to be grown were selected on the hygromycin plate, and were planted in soil and grown.

(6-3) Traits of Plants Transformed with pCUC2-36RD

E of FIG. 4 shows the trait of the seedling of the plant transformed with pCUC2-36RD. Typically, the seedling of *Arabidopsis thaliana* exhibits the morphology like "mustard and cress", i.e., two independent cotyledons. However, the seedlings of the plants transformed with pCUC2-36RD were confirmed to exhibit the morphology of cotyledons that were partially or wholly fused (so-called cup-like shape). Furthermore, there existed an individual in which the apical meristem of shoot was not formed. This morphology is quite similar to those of (i) the seedling of the plant transformed with pCUC2-SRDX (shown in D of FIG. 4) and (ii) the cuc1/cuc2 double deletion mutant.

These results demonstrate the following facts: (i) a peptide including the amino acid sequence encoded by 36RD (GN-SKTLRLFGVNMEC, SEQ ID NO: 3) and (ii) a gene encoding the peptide each have ability to convert any transcription factor into a transcriptional repressor; and the chimeric protein thus obtained acts dominantly over endogenous redundant genes.

All of the publications, patents, and patent applications cited herein are incorporated herein by reference.

INDUSTRIAL APPLICABILITY

A peptide encoded by a gene of the present invention is capable of repressing transcription of a certain target gene only, as known peptides capable of repressing transcription are. Therefore, the peptide of the present invention is expected to be applied to the breeding of various plants, as well as known peptide genes capable of repressing transcription. In addition, the peptide of the present invention has a conserved motif which is completely different from those of the known peptides. Therefore, the peptide of the present invention will be applied to wider range of fields and will provide useful technical means either by using it solely or in combination with any of the known peptides.

The invention claimed is:

1. An isolated chimeric protein which is capable of repressing transcription, comprising:
   a peptide capable of repressing transcription in a plant, consisting of the amino acid sequence of SEQ ID NO: 78 and
   a transcription factor or its DNA-binding domain, wherein said transcription factor or its DNA-binding domain is heterologous to said peptide,
   wherein the peptide is operably linked to the transcription factor or its DNA-binding domain.

2. An isolated nucleic acid molecule encoding a chimeric protein which is capable of repressing transcription, comprising:
   a first nucleic acid sequence encoding a peptide which is capable of repressing transcription in a plant; and
   a second nucleic acid sequence encoding a transcription factor or its DNA-binding domain, wherein said transcription factor or its DNA-binding domain is heterologous to said peptide, wherein
   the first nucleic acid sequence being linked in frame with the second nucleic acid sequence, wherein
   the peptide consists of the amino acid sequence of SEQ ID NO: 78.

3. An expression vector comprising the isolated nucleic acid molecule as set forth in claim 2.

4. A plant transformed with the isolated nucleic acid molecule as set forth in claim 2, wherein said plant expresses said nucleic acid molecule.

5. A method for producing a chimeric protein which is capable of repressing transcription, comprising the steps of:
   transforming cells with an expression vector comprising the isolated nucleic acid molecule as set forth in claim 2;
   culturing the cells thus transformed, in order to obtain an expression product from the expression vector;
   collecting the expression product; and
   purifying the expression product.

6. The isolated chimeric protein as set forth in claim 1, wherein:

said peptide consists of an amino acid sequence selected from the group consisting of SEQ ID NOs: 3 to 33.

7. The isolated nucleic acid of claim 2, wherein said encoded peptide consists of an amino acid sequence selected from the group consisting of SEQ ID NOs: 3 to 33.

* * * * *

```
SEQUENCE LISTING

<160> NUMBER OF SEQ ID NOS: 79

<210> SEQ ID NO 1
<211> LENGTH: 7
<212> TYPE: PRT
<213> ORGANISM: Artificial
<220> FEATURE:
<223> OTHER INFORMATION: repression domain 1
<220> FEATURE:
<221> NAME/KEY: MISC_FEATURE
<222> LOCATION: (1)..(7)
<223> OTHER INFORMATION: Xaa=any amino acid

<400> SEQUENCE: 1

Xaa Arg Leu Phe Gly Val Xaa
1               5

<210> SEQ ID NO 2
<211> LENGTH: 7
<212> TYPE: PRT
<213> ORGANISM: Artificial
<220> FEATURE:
<223> OTHER INFORMATION: repression domain 2
<220> FEATURE:
<221> NAME/KEY: MISC_FEATURE
<222> LOCATION: (1)..(7)
<223> OTHER INFORMATION: Xaa=any amino acid

<400> SEQUENCE: 2

Xaa Lys Leu Phe Gly Val Xaa
1               5

<210> SEQ ID NO 3
<211> LENGTH: 15
<212> TYPE: PRT
<213> ORGANISM: Artificial
<220> FEATURE:
<223> OTHER INFORMATION: At2g36080.1-peptide

<400> SEQUENCE: 3

Gly Asn Ser Lys Thr Leu Arg Leu Phe Gly Val Asn Met Glu Cys
1               5                   10                  15

<210> SEQ ID NO 4
<211> LENGTH: 15
<212> TYPE: PRT
<213> ORGANISM: Artificial
<220> FEATURE:
<223> OTHER INFORMATION: At3g11580.1-peptide

<400> SEQUENCE: 4

Gly Ser Ser Arg Thr Val Arg Leu Phe Gly Val Asn Leu Glu Cys
1               5                   10                  15
```

```
<210> SEQ ID NO 5
<211> LENGTH: 15
<212> TYPE: PRT
<213> ORGANISM: Artificial
<220> FEATURE:
<223> OTHER INFORMATION: At5g06250-peptide

<400> SEQUENCE: 5

Gly Ser Ser Arg Thr Val Arg Leu Phe Gly Val Asn Leu Glu Cys
1               5                   10                  15

<210> SEQ ID NO 6
<211> LENGTH: 15
<212> TYPE: PRT
<213> ORGANISM: Artificial
<220> FEATURE:
<223> OTHER INFORMATION: At2g46870-peptide

<400> SEQUENCE: 6

Thr Ala Gly Lys Arg Leu Arg Leu Phe Gly Val Asp Met Glu Cys
1               5                   10                  15

<210> SEQ ID NO 7
<211> LENGTH: 15
<212> TYPE: PRT
<213> ORGANISM: Artificial
<220> FEATURE:
<223> OTHER INFORMATION: At1g01030-peptide

<400> SEQUENCE: 7

Thr Ala Gly Lys Arg Leu Arg Leu Phe Gly Val Asn Met Glu Cys
1               5                   10                  15

<210> SEQ ID NO 8
<211> LENGTH: 15
<212> TYPE: PRT
<213> ORGANISM: Artificial
<220> FEATURE:
<223> OTHER INFORMATION: At3g61970-peptide

<400> SEQUENCE: 8

Arg Gly Glu Lys Arg Leu Arg Leu Phe Gly Val Asp Met Glu Cys
1               5                   10                  15

<210> SEQ ID NO 9
<211> LENGTH: 15
<212> TYPE: PRT
<213> ORGANISM: Artificial
<220> FEATURE:
<223> OTHER INFORMATION: At4g01500-peptide

<400> SEQUENCE: 9

Ser Thr Thr Lys Lys Leu Arg Leu Phe Gly Val Asp Val Glu Glu
1               5                   10                  15

<210> SEQ ID NO 10
<211> LENGTH: 15
<212> TYPE: PRT
<213> ORGANISM: Artificial
<220> FEATURE:
<223> OTHER INFORMATION: At1g13260-peptide

<400> SEQUENCE: 10

Asp Ala Gly Arg Val Leu Arg Leu Phe Gly Val Asn Ile Ser Pro
1               5                   10                  15
```

```
<210> SEQ ID NO 11
<211> LENGTH: 15
<212> TYPE: PRT
<213> ORGANISM: Artificial
<220> FEATURE:
<223> OTHER INFORMATION: At1g68840-peptide

<400> SEQUENCE: 11

Pro Val Gln Val Val Arg Leu Phe Gly Val Asp Ile Phe Asn
1               5                   10                  15

<210> SEQ ID NO 12
<211> LENGTH: 15
<212> TYPE: PRT
<213> ORGANISM: Artificial
<220> FEATURE:
<223> OTHER INFORMATION: At3g25730-peptide

<400> SEQUENCE: 12

Glu Thr Gly Arg Val Met Arg Leu Phe Gly Val Asp Ile Ser Leu
1               5                   10                  15

<210> SEQ ID NO 13
<211> LENGTH: 15
<212> TYPE: PRT
<213> ORGANISM: Artificial
<220> FEATURE:
<223> OTHER INFORMATION: At1g25560-peptide

<400> SEQUENCE: 13

Pro Val Gln Thr Val Val Arg Leu Phe Gly Val Asn Ile Phe Asn
1               5                   10                  15

<210> SEQ ID NO 14
<211> LENGTH: 15
<212> TYPE: PRT
<213> ORGANISM: Artificial
<220> FEATURE:
<223> OTHER INFORMATION: At1g35240-peptide

<400> SEQUENCE: 14

Lys Ala Val Thr Asn Phe Arg Leu Phe Gly Val Ser Leu Ala Ile
1               5                   10                  15

<210> SEQ ID NO 15
<211> LENGTH: 15
<212> TYPE: PRT
<213> ORGANISM: Artificial
<220> FEATURE:
<223> OTHER INFORMATION: At1g34310-peptide

<400> SEQUENCE: 15

Lys Thr Gly Thr Asn Phe Arg Leu Phe Gly Val Thr Leu Asp Thr
1               5                   10                  15

<210> SEQ ID NO 16
<211> LENGTH: 15
<212> TYPE: PRT
<213> ORGANISM: Artificial
<220> FEATURE:
<223> OTHER INFORMATION: At1g34390-peptide

<400> SEQUENCE: 16

Lys Thr Gly Thr Asn Phe Arg Leu Phe Gly Val Ser Leu Val Thr
1               5                   10                  15
```

```
<210> SEQ ID NO 17
<211> LENGTH: 15
<212> TYPE: PRT
<213> ORGANISM: Artificial
<220> FEATURE:
<223> OTHER INFORMATION: At1g34410-peptide

<400> SEQUENCE: 17

Lys Ala Gly Thr Asn Phe Arg Leu Phe Gly Val Thr Leu Asp Thr
1               5                   10                  15

<210> SEQ ID NO 18
<211> LENGTH: 15
<212> TYPE: PRT
<213> ORGANISM: Artificial
<220> FEATURE:
<223> OTHER INFORMATION: At1g35520-peptide

<400> SEQUENCE: 18

Lys Ala Gly Thr Asn Phe Arg Leu Phe Gly Val Ser Leu Ala Thr
1               5                   10                  15

<210> SEQ ID NO 19
<211> LENGTH: 15
<212> TYPE: PRT
<213> ORGANISM: Artificial
<220> FEATURE:
<223> OTHER INFORMATION: At1g35540-peptide

<400> SEQUENCE: 19

Asn Ala Val Ala Ser Phe Arg Leu Phe Gly Val Ser Leu Ala Thr
1               5                   10                  15

<210> SEQ ID NO 20
<211> LENGTH: 15
<212> TYPE: PRT
<213> ORGANISM: Artificial
<220> FEATURE:
<223> OTHER INFORMATION: At4g36990-peptide

<400> SEQUENCE: 20

Gly Val Gly Glu Gly Leu Lys Leu Phe Gly Val Trp Leu Lys Gly
1               5                   10                  15

<210> SEQ ID NO 21
<211> LENGTH: 15
<212> TYPE: PRT
<213> ORGANISM: Artificial
<220> FEATURE:
<223> OTHER INFORMATION: At5g62020-peptide

<400> SEQUENCE: 21

Glu Glu Glu Ala Ser Pro Arg Leu Phe Gly Val Pro Ile Gly Leu
1               5                   10                  15

<210> SEQ ID NO 22
<211> LENGTH: 15
<212> TYPE: PRT
<213> ORGANISM: Artificial
<220> FEATURE:
<223> OTHER INFORMATION: At4g11660-peptide

<400> SEQUENCE: 22

Gly Glu Asp Leu Thr Pro Arg Leu Phe Gly Val Ser Ile Gly Val
1               5                   10                  15
```

```
<210> SEQ ID NO 23
<211> LENGTH: 14
<212> TYPE: PRT
<213> ORGANISM: Artificial
<220> FEATURE:
<223> OTHER INFORMATION: At2g41690-peptide

<400> SEQUENCE: 23

Glu Glu Asp Glu Gly Leu Lys Leu Phe Gly Val Lys Leu Glu
1               5                   10

<210> SEQ ID NO 24
<211> LENGTH: 15
<212> TYPE: PRT
<213> ORGANISM: Artificial
<220> FEATURE:
<223> OTHER INFORMATION: At1g46264-peptide

<400> SEQUENCE: 24

Ser Asn Met Arg Lys Thr Lys Leu Phe Gly Val Ser Leu Pro Ser
1               5                   10                  15

<210> SEQ ID NO 25
<211> LENGTH: 15
<212> TYPE: PRT
<213> ORGANISM: Artificial
<220> FEATURE:
<223> OTHER INFORMATION: At3g16350-peptide

<400> SEQUENCE: 25

Gly Ser Ser Ser Ala Val Lys Leu Phe Gly Val Arg Leu Thr Asp
1               5                   10                  15

<210> SEQ ID NO 26
<211> LENGTH: 15
<212> TYPE: PRT
<213> ORGANISM: Artificial
<220> FEATURE:
<223> OTHER INFORMATION: At5g47390-peptide

<400> SEQUENCE: 26

Cys Pro Asn Arg Gly Val Lys Leu Phe Gly Val Arg Leu Thr Glu
1               5                   10                  15

<210> SEQ ID NO 27
<211> LENGTH: 15
<212> TYPE: PRT
<213> ORGANISM: Artificial
<220> FEATURE:
<223> OTHER INFORMATION: At5g56840-peptide

<400> SEQUENCE: 27

Tyr Gln Thr Arg Val Val Arg Leu Phe Gly Val His Leu Asp Thr
1               5                   10                  15

<210> SEQ ID NO 28
<211> LENGTH: 15
<212> TYPE: PRT
<213> ORGANISM: Artificial
<220> FEATURE:
<223> OTHER INFORMATION: At5g61620-peptide

<400> SEQUENCE: 28

Val Asn Lys Ala Ser Val Lys Leu Phe Gly Val Asn Ile Ser Ser
1               5                   10                  15
```

-continued

```
<210> SEQ ID NO 29
<211> LENGTH: 14
<212> TYPE: PRT
<213> ORGANISM: Artificial
<220> FEATURE:
<223> OTHER INFORMATION: At1g30810-peptide

<400> SEQUENCE: 29

Ala Ser Leu Thr Lys Gly Lys Leu Phe Gly Val Asp Leu Met
1               5                   10

<210> SEQ ID NO 30
<211> LENGTH: 14
<212> TYPE: PRT
<213> ORGANISM: Artificial
<220> FEATURE:
<223> OTHER INFORMATION: At2g34880-peptide

<400> SEQUENCE: 30

Gln Ser Leu Ser Lys Ala Arg Leu Phe Gly Val Asp Leu Asn
1               5                   10

<210> SEQ ID NO 31
<211> LENGTH: 14
<212> TYPE: PRT
<213> ORGANISM: Artificial
<220> FEATURE:
<223> OTHER INFORMATION: At2g37650-peptide

<400> SEQUENCE: 31

Arg Leu Ala Ala Tyr Ala Lys Leu Phe Gly Val Pro Phe Glu
1               5                   10

<210> SEQ ID NO 32
<211> LENGTH: 8
<212> TYPE: PRT
<213> ORGANISM: Artificial
<220> FEATURE:
<223> OTHER INFORMATION: At2g36080.1-peptide(2)

<400> SEQUENCE: 32

Leu Arg Leu Phe Gly Val Asn Met
1               5

<210> SEQ ID NO 33
<211> LENGTH: 11
<212> TYPE: PRT
<213> ORGANISM: Artificial
<220> FEATURE:
<223> OTHER INFORMATION: At4g36990-peptide(2)

<400> SEQUENCE: 33

Gly Glu Gly Leu Lys Leu Phe Gly Val Trp Leu
1               5                   10

<210> SEQ ID NO 34
<211> LENGTH: 30
<212> TYPE: DNA
<213> ORGANISM: Artificial
<220> FEATURE:
<223> OTHER INFORMATION: At2g36080(1-29)primer1

<400> SEQUENCE: 34
gatgtcaata aaccaatact caagcgattt                                     30
```

<210> SEQ ID NO 35
<211> LENGTH: 37
<212> TYPE: DNA
<213> ORGANISM: Artificial
<220> FEATURE:
<223> OTHER INFORMATION: At2g36080(710-735)primer

<400> SEQUENCE: 35
gtcgacgtcg acttagctcg tccggttcat atctcct                         37

<210> SEQ ID NO 36
<211> LENGTH: 30
<212> TYPE: DNA
<213> ORGANISM: Artificial
<220> FEATURE:
<223> OTHER INFORMATION: At2g36080(491-506)primer

<400> SEQUENCE: 36
aataaaaagg gtacctgcat gaggataata                                 30

<210> SEQ ID NO 37
<211> LENGTH: 30
<212> TYPE: DNA
<213> ORGANISM: Artificial
<220> FEATURE:
<223> OTHER INFORMATION: At2g36080(511-531)primer3

<400> SEQUENCE: 37
agatctagat ctttggctct ccaccgcttg                                 30

<210> SEQ ID NO 38
<211> LENGTH: 32
<212> TYPE: DNA
<213> ORGANISM: Artificial
<220> FEATURE:
<223> OTHER INFORMATION: At2g36080(577-598)primer2

<400> SEQUENCE: 38
agatctagat ctcagctaga ttcggactgg tc                              32

<210> SEQ ID NO 39
<211> LENGTH: 49
<212> TYPE: DNA
<213> ORGANISM: Artificial
<220> FEATURE:
<223> OTHER INFORMATION: At2g36080(532-576)s

<400> SEQUENCE: 39
aggcaactcg aagacattaa gactgttcgg agtgaacatg gagtgctaa            49

<210> SEQ ID NO 40
<211> LENGTH: 49
<212> TYPE: DNA
<213> ORGANISM: Artificial
<220> FEATURE:
<223> OTHER INFORMATION: At2g36080(532-576)a

<400> SEQUENCE: 40
ttagcactcc atgttcactc cgaacagtct taatgtcttc gagttgcct            49

<210> SEQ ID NO 41
<211> LENGTH: 65
<212> TYPE: DNA
<213> ORGANISM: Artificial
<220> FEATURE:
<223> OTHER INFORMATION: CaMV35SpromoterDNA1

<400> SEQUENCE: 41
agcttagatc tgcaagaccc ttcctctata taaggaagtt catttcattt ggagaggaca    60
cgctg    65

<210> SEQ ID NO 42
<211> LENGTH: 65
<212> TYPE: DNA
<213> ORGANISM: Artificial
<220> FEATURE:
<223> OTHER INFORMATION: CaMV35SpromoterDNA2

<400> SEQUENCE: 42
gatccagcgt gtcctctcca aatgaaatga acttccttat atagaggaag ggtcttgcag    60
atcta    65

<210> SEQ ID NO 43
<211> LENGTH: 34
<212> TYPE: DNA
<213> ORGANISM: Artificial
<220> FEATURE:
<223> OTHER INFORMATION: CaMV35Spromoter(-800to-46)5'primer

<400> SEQUENCE: 43
attcccaagc ttcggataac aatttcacac agga    34

<210> SEQ ID NO 44
<211> LENGTH: 37
<212> TYPE: DNA
<213> ORGANISM: Artificial
<220> FEATURE:
<223> OTHER INFORMATION: CaMV35Spromoter(-800to-46)3'primer

<400> SEQUENCE: 44
aagggtaagc ttaaggatag tgggattgtg cgtcatc    37

<210> SEQ ID NO 45
<211> LENGTH: 27
<212> TYPE: DNA
<213> ORGANISM: Artificial
<220> FEATURE:
<223> OTHER INFORMATION: At2g36080(547-576)s

<400> SEQUENCE: 45
ttaagactgt tcggagtgaa catgtaa    27

<210> SEQ ID NO 46
<211> LENGTH: 27
<212> TYPE: DNA
<213> ORGANISM: Artificial
<220> FEATURE:
<223> OTHER INFORMATION: At2g36080(547-576)a

<400> SEQUENCE: 46
ttacatgttc actccgaaca gtcttaa    27

<210> SEQ ID NO 47
<211> LENGTH: 30
<212> TYPE: DNA
<213> ORGANISM: Artificial
<220> FEATURE:
<223> OTHER INFORMATION: At3g11580(1-29)primer

<400> SEQUENCE: 47
gatgtcagtc aaccattacc acaacactct    30

```
<210> SEQ ID NO 48
<211> LENGTH: 36
<212> TYPE: DNA
<213> ORGANISM: Artificial
<220> FEATURE:
<223> OTHER INFORMATION: At3g11580(775-804)primer

<400> SEQUENCE: 48
gtcgacgtcg actcaacctc gtccatctcc tacctg                                36

<210> SEQ ID NO 49
<211> LENGTH: 30
<212> TYPE: DNA
<213> ORGANISM: Artificial
<220> FEATURE:
<223> OTHER INFORMATION: At2g46870(1-29)primer

<400> SEQUENCE: 49
gatgatgaca gatttatctc tcacgagaga                                       30

<210> SEQ ID NO 50
<211> LENGTH: 24
<212> TYPE: DNA
<213> ORGANISM: Artificial
<220> FEATURE:
<223> OTHER INFORMATION: At2g46870(910-933)primer

<400> SEQUENCE: 50
ttattgatcc aaatcaaaag acaa                                             24

<210> SEQ ID NO 51
<211> LENGTH: 23
<212> TYPE: DNA
<213> ORGANISM: Artificial
<220> FEATURE:
<223> OTHER INFORMATION: At1g13260(1-29)primer

<400> SEQUENCE: 51
gatggaatcg agtagcgttg atg                                              23

<210> SEQ ID NO 52
<211> LENGTH: 24
<212> TYPE: DNA
<213> ORGANISM: Artificial
<220> FEATURE:
<223> OTHER INFORMATION: At1g13260(1012-1035)primer

<400> SEQUENCE: 52
ttacgaggcg tgaaagatgc gttg                                             24

<210> SEQ ID NO 53
<211> LENGTH: 23
<212> TYPE: DNA
<213> ORGANISM: Artificial
<220> FEATURE:
<223> OTHER INFORMATION: At1g68840(1-22)primer

<400> SEQUENCE: 53
gatggattct agttgcatag acg                                              23

<210> SEQ ID NO 54
<211> LENGTH: 25
<212> TYPE: DNA
<213> ORGANISM: Artificial
<220> FEATURE:
<223> OTHER INFORMATION: At1g68840(1035-1059)primer
```

<400> SEQUENCE: 54
ttacaaagca ttgattatcg cctgc                                    25

<210> SEQ ID NO 55
<211> LENGTH: 30
<212> TYPE: DNA
<213> ORGANISM: Artificial
<220> FEATURE:
<223> OTHER INFORMATION: At4g36990(1-29)primer

<400> SEQUENCE: 55
gatgacggct gtgacggcgg cgcaaagatc                               30

<210> SEQ ID NO 56
<211> LENGTH: 45
<212> TYPE: DNA
<213> ORGANISM: Artificial
<220> FEATURE:
<223> OTHER INFORMATION: At4g36990(823-855)primer

<400> SEQUENCE: 56
gtcgacgtcg acttagttgc agactttgct gcttttccac aacgg              45

<210> SEQ ID NO 57
<211> LENGTH: 30
<212> TYPE: DNA
<213> ORGANISM: Artificial
<220> FEATURE:
<223> OTHER INFORMATION: At4g11660(1-29)primer

<400> SEQUENCE: 57
gatgccgggg gaacaaaccg gagaaactcc                               30

<210> SEQ ID NO 58
<211> LENGTH: 39
<212> TYPE: DNA
<213> ORGANISM: Artificial
<220> FEATURE:
<223> OTHER INFORMATION: At4g11660(1108-1134)primer

<400> SEQUENCE: 58
gtcgacgtcg actcattttc cgagttcaag ccacgaccc                     39

<210> SEQ ID NO 59
<211> LENGTH: 46
<212> TYPE: DNA
<213> ORGANISM: Artificial
<220> FEATURE:
<223> OTHER INFORMATION: At4g36990(697-729)s

<400> SEQUENCE: 59
gggtgaagga ttgaaattgt ttggggtgtg gttggtcgac gtcgac             46

<210> SEQ ID NO 60
<211> LENGTH: 46
<212> TYPE: DNA
<213> ORGANISM: Artificial
<220> FEATURE:
<223> OTHER INFORMATION: At4g36990(697-729)a

<400> SEQUENCE: 60
gtcgacgtcg accaaccaca ccccaaacaa tttcaatcct tcaccc             46

```
<210> SEQ ID NO 61
<211> LENGTH: 41
<212> TYPE: DNA
<213> ORGANISM: Artificial
<220> FEATURE:
<223> OTHER INFORMATION: At4g36990(680-705)primer2

<400> SEQUENCE: 61 cccccccgcgg ctccagctcc ttcacctacc ccctcctctg c          41

<210> SEQ ID NO 62
<211> LENGTH: 42
<212> TYPE: DNA
<213> ORGANISM: Artificial
<220> FEATURE:
<223> OTHER INFORMATION: At4g36990(732-752)primer2

<400> SEQUENCE: 62
gggccgcggg ggcttgggct aaaggagaga gaaaaaagag gg          42

<210> SEQ ID NO 63
<211> LENGTH: 76
<212> TYPE: DNA
<213> ORGANISM: Artificial
<220> FEATURE:
<223> OTHER INFORMATION: pBIG2(omega)s

<400> SEQUENCE: 63
gatccacaat taccaacaac aacaaacaac aaacaacatt acaattacag atcccggggg     60
taccgtcgac gagctc                                                    76

<210> SEQ ID NO 64
<211> LENGTH: 66
<212> TYPE: DNA
<213> ORGANISM: Artificial
<220> FEATURE:
<223> OTHER INFORMATION: pBIG2(omega)a

<400> SEQUENCE: 64
cgtcgacggt accccgggga tctgtaattg taatgttgtt tgttgtttgt tgttgttggt     60
aattgt                                                               66

<210> SEQ ID NO 65
<211> LENGTH: 52
<212> TYPE: DNA
<213> ORGANISM: Artificial
<220> FEATURE:
<223> OTHER INFORMATION: At2g36080(532-576)s

<400> SEQUENCE: 65
gggaggcaac tcgaagacat taagactgtt cggagtgaac atggagtgct aa             52

<210> SEQ ID NO 66
<211> LENGTH: 52
<212> TYPE: DNA
<213> ORGANISM: Artificial
<220> FEATURE:
<223> OTHER INFORMATION: At2g36080(532-576)a

<400> SEQUENCE: 66
ttagcactcc atgttcactc cgaacagtct taatgtcttc gagttgcctc cc             52
```

-continued

```
<210> SEQ ID NO 67
<211> LENGTH: 30
<212> TYPE: DNA
<213> ORGANISM: Artificial
<220> FEATURE:
<223> OTHER INFORMATION: AGAMOUS(1-759)5'primer

<400> SEQUENCE: 67
gatgaccgcg taccaatcgg agctaggagg                                   30

<210> SEQ ID NO 68
<211> LENGTH: 30
<212> TYPE: DNA
<213> ORGANISM: Artificial
<220> FEATURE:
<223> OTHER INFORMATION: AGAMOUS(1-759)5'primer

<400> SEQUENCE: 68
cactaactgg agagcggttt ggtcttggcg                                   30

<210> SEQ ID NO 69
<211> LENGTH: 27
<212> TYPE: DNA
<213> ORGANISM: Artificial
<220> FEATURE:
<223> OTHER INFORMATION: At2g36080(532-576)5'primer

<400> SEQUENCE: 69
gggatggaca ttccgtatta ccactac                                      27

<210> SEQ ID NO 70
<211> LENGTH: 23
<212> TYPE: DNA
<213> ORGANISM: Artificial
<220> FEATURE:
<223> OTHER INFORMATION: At2g36080(532-576)3'primer

<400> SEQUENCE: 70
gtagttccaa atacagtcaa gtc                                          23

<210> SEQ ID NO 71
<211> LENGTH: 11
<212> TYPE: PRT
<213> ORGANISM: Artificial
<220> FEATURE:
<223> OTHER INFORMATION: mutated amino acids

<400> SEQUENCE: 71

Gly Glu Gly Ala Gly Ala Ala Gly Ala Trp Ala
1               5                   10

<210> SEQ ID NO 72
<211> LENGTH: 10
<212> TYPE: PRT
<213> ORGANISM: Artificial
<220> FEATURE:
<223> OTHER INFORMATION: repression domain

<400> SEQUENCE: 72

Leu Asp Leu Glu Leu Arg Leu Gly Phe Ala
1               5                   10

<210> SEQ ID NO 73
<211> LENGTH: 7
<212> TYPE: PRT
<213> ORGANISM: Artificial
```

```
<220> FEATURE:
<223> OTHER INFORMATION: motif
<220> FEATURE:
<221> NAME/KEY: MISC_FEATURE
<222> LOCATION: (1)..(1)
<223> OTHER INFORMATION: Xaa=Leu or Phe
<220> FEATURE:
<221> NAME/KEY: MISC_FEATURE
<222> LOCATION: (5)..(5)
<223> OTHER INFORMATION: Xaa=Leu or Phe
<220> FEATURE:
<221> NAME/KEY: MISC_FEATURE
<222> LOCATION: (6)..(6)
<223> OTHER INFORMATION: Xaa=any amino acid

<400> SEQUENCE: 73

Xaa Asp Leu Asn Xaa Xaa Pro
1               5

<210> SEQ ID NO 74
<211> LENGTH: 6
<212> TYPE: PRT
<213> ORGANISM: Artificial
<220> FEATURE:
<223> OTHER INFORMATION: motif

<400> SEQUENCE: 74

Asp Leu Glu Leu Arg Leu
1               5

<210> SEQ ID NO 75
<211> LENGTH: 5
<212> TYPE: PRT
<213> ORGANISM: Artificial
<220> FEATURE:
<223> OTHER INFORMATION: motif

<400> SEQUENCE: 75

Arg Leu Phe Gly Val
1               5

<210> SEQ ID NO 76
<211> LENGTH: 5
<212> TYPE: PRT
<213> ORGANISM: Artificial
<220> FEATURE:
<223> OTHER INFORMATION: motif

<400> SEQUENCE: 76

Lys Leu Phe Gly Val
1               5

<210> SEQ ID NO 77
<211> LENGTH: 5
<212> TYPE: PRT
<213> ORGANISM: Artificial
<220> FEATURE:
<223> OTHER INFORMATION: motif
<220> FEATURE:
<221> NAME/KEY: MISC_FEATURE
<222> LOCATION: (1)..(1)
<223> OTHER INFORMATION: Xaa=Arg or Lys

<400> SEQUENCE: 77

Xaa Leu Phe Gly Val
1               5
```

```
<210> SEQ ID NO 78
<211> LENGTH: 25
<212> TYPE: PRT
<213> ORGANISM: Artificial
<220> FEATURE:
<223> OTHER INFORMATION: repression domain
<220> FEATURE:
<221> NAME/KEY: MISC_FEATURE
<222> LOCATION: (1)..(10)
<223> OTHER INFORMATION: Xaa=any amino acid and up to nine of them may
      be absent
<220> FEATURE:
<221> NAME/KEY: MISC_FEATURE
<222> LOCATION: (11)..(11)
<223> OTHER INFORMATION: Xaa=Arg or Lys
<220> FEATURE:
<221> NAME/KEY: MISC_FEATURE
<222> LOCATION: (16)..(25)
<223> OTHER INFORMATION: Xaa=any amino acid and up to nine of them may
      be absent

<400> SEQUENCE: 78

Xaa Xaa Xaa Xaa Xaa Xaa Xaa Xaa Xaa Xaa Xaa Leu Phe Gly Val Xaa
1               5                   10                  15

Xaa Xaa Xaa Xaa Xaa Xaa Xaa Xaa Xaa
                20                  25

<210> SEQ ID NO 79
<211> LENGTH: 15
<212> TYPE: PRT
<213> ORGANISM: Artificial
<220> FEATURE:
<223> OTHER INFORMATION: repression domain
<220> FEATURE:
<221> NAME/KEY: MISC_FEATURE
<222> LOCATION: (1)..(5)
<223> OTHER INFORMATION: Xaa=any amino acid and up to four of them may
      be absent
<220> FEATURE:
<221> NAME/KEY: MISC_FEATURE
<222> LOCATION: (6)..(6)
<223> OTHER INFORMATION: Xaa=Arg or Lys
<220> FEATURE:
<221> NAME/KEY: MISC_FEATURE
<222> LOCATION: (11)..(15)
<223> OTHER INFORMATION: Xaa=any amino acid and up to four of them may
      be absent

<400> SEQUENCE: 79

Xaa Xaa Xaa Xaa Xaa Xaa Leu Phe Gly Val Xaa Xaa Xaa Xaa Xaa
1               5                   10                  15
```